(12) United States Patent
Ren et al.

(10) Patent No.: US 12,409,053 B2
(45) Date of Patent: Sep. 9, 2025

(54) DEGRADABLE BIOMEDICAL MAGNESIUM ALLOY DRUG-ELUTING VASCULAR STENT AND PREPARATION METHOD

(71) Applicant: AmsinoMed Medical Co., Ltd, Beijing (CN)

(72) Inventors: Hefei Ren, Beijing (CN); Xin Shen, Beijing (CN); Dongyun Hao, Beijing (CN); Yanan Li, Beijing (CN); Jia She, Beijing (CN); Fusheng Pan, Beijing (CN); Fugui He, Beijing (CN); Xiaoyi Ma, Beijing (CN); Lifeng Zhou, Beijing (CN)

(73) Assignee: AmsinoMed Medical Co., Ltd, Beijing (CN)

(*) Notice: Subject to any disclaimer, the term of this patent is extended or adjusted under 35 U.S.C. 154(b) by 0 days.

(21) Appl. No.: 18/804,861

(22) Filed: Aug. 14, 2024

(65) Prior Publication Data
US 2024/0398593 A1    Dec. 5, 2024

Related U.S. Application Data

(63) Continuation of application No. PCT/CN2022/133109, filed on Nov. 21, 2022.

(30) Foreign Application Priority Data

Feb. 14, 2022 (CN) .......................... 202210131931.X

(51) Int. Cl.
*A61F 2/915* (2013.01)
*A61L 31/08* (2006.01)

(52) U.S. Cl.
CPC .... *A61F 2/915* (2013.01); *A61F 2002/91575* (2013.01); *A61F 2210/0004* (2013.01);
(Continued)

(58) Field of Classification Search
CPC ........ A61L 31/022; A61L 31/08; A61L 31/16; A61F 2/915; A61F 2210/0076; A61F 2250/0039; A61F 2250/0036
See application file for complete search history.

(56) References Cited

U.S. PATENT DOCUMENTS

2007/0135908 A1    6/2007  Zhao
2007/0283552 A1*  12/2007  Gale .................. A61F 2/915
                                                    29/515
(Continued)

FOREIGN PATENT DOCUMENTS

CN    101147814 A    3/2008
CN    101214396 A    7/2008
(Continued)

OTHER PUBLICATIONS

Translation of CN 110983135 (Year: 2020).*
(Continued)

*Primary Examiner* — Brian E Pellegrino
(74) *Attorney, Agent, or Firm* — Hamilton, Brook, Smith & Reynolds, P.C.

(57) ABSTRACT

A degradable biomedical magnesium alloy drug-eluting vascular stent and a preparation method. With the total weight of a magnesium alloy being 100% for calculation, the magnesium alloy comprises the following components in percentage by weight: 3.0-6.0% of Gd, 2.5-5.5% of Y, 1.0-3.0% of Li, 0.3-1.0% of Zn, 0.2-1.0% of Zr, and the balance being Mg. The stent has good radial support strength and strain dispersion capability by means of finite element design. After a protective coating is used, the corrosion resistance of the magnesium alloy stent is greatly improved. An arsenic trioxide/rapamycin and tacrolimus composite drug sustained-release system is used to fully adapt to the damage repair process of blood vessels. An implantation
(Continued)

result of large animals shows that the vascular stent system has a good anti-restenosis treatment effect.

19 Claims, 11 Drawing Sheets

(52) U.S. Cl.
CPC .......... *A61F 2210/0009* (2013.01); *A61F 2210/0076* (2013.01); *A61F 2230/0006* (2013.01); *A61F 2230/0069* (2013.01); *A61F 2240/001* (2013.01); *A61F 2250/0039* (2013.01); *A61F 2250/0067* (2013.01)

(56) References Cited

U.S. PATENT DOCUMENTS

| | | | |
|---|---|---|---|
| 2016/0262915 A1* | 9/2016 | Mangiardi | A61L 31/022 623/1.15 |
| 2018/0264180 A1 | 9/2018 | Sasaki et al. | |
| 2019/0153570 A1 | 5/2019 | Zhou et al. | |
| 2020/0139017 A1 | 5/2020 | Meyer-Kobbe et al. | |
| 2024/0207075 A1 | 6/2024 | Bian et al. | |

FOREIGN PATENT DOCUMENTS

| | | | | |
|---|---|---|---|---|
| CN | 204600807 U | | 9/2015 | |
| CN | 105671391 A | | 6/2016 | |
| CN | 108289747 A | | 7/2017 | |
| CN | 107088110 A | | 8/2017 | |
| CN | 107630157 A | | 1/2018 | |
| CN | 108315618 A | | 7/2018 | |
| CN | 110983135 A | * | 4/2020 | .......... A61L 31/022 |
| CN | 113116595 A | | 7/2021 | |
| CN | 114159197 A | | 3/2022 | |
| WO | WO-9858600 A1 | * | 12/1998 | .............. A61F 2/91 |
| WO | WO-0042946 A1 | * | 7/2000 | .............. A61F 2/91 |
| WO | WO-2008061017 A1 | * | 5/2008 | .............. A61F 2/06 |
| WO | WO-2009031295 A1 | * | 3/2009 | .............. A61F 2/82 |
| WO | WO-2019176725 A1 | * | 9/2019 | |

OTHER PUBLICATIONS

Translation of CN 113116595 (Year: 2021).*
International Search Report for International Application No. PCT/CN2022/133109, "Degradable Biomedical Magnesium Alloy Drug-Eluting Vascular Stent and Preparation Method" dated Jan. 16, 2023.
Chinese Search Report for Chinese Application No. 202210131931X, "Degradable Biomedical Magnesium Alloy Drug-Eluting Vascular Stent and Preparation Method", dated Mar. 21, 2022.
Supplemental Chinese Search Report for Chinese Application No. 202210131931X, "Degradable Biomedical Magnesium Alloy Drug-Eluting Vascular Stent and Preparation Method", dated Apr. 13, 2022 . . . .
Supplementary European Search Report for EP Application No. 22925694, "Degradable Biomedical Magnesium Alloy Drug-Eluting Vascular Stent and Preparation Method" dated May 16, 2025.

* cited by examiner

DEGRADABLE BIOMEDICAL MAGNESIUM ALLOY DRUG-ELUTING VASCULAR STENT AND PREPARATION METHOD

RELATED APPLICATIONS

This application is a continuation of International Application No. PCT/CN2022/133109, filed Nov. 21, 2022, which designates the U.S., published in Chinese, and claims priority under 35 U.S.C. § 119 or 365(c) to Chinese Application No. 202210131931.X, filed Feb. 14, 2022. The entire teachings of the above applications are incorporated herein by reference.

FIELD OF THE INVENTION

The present invention relates to the field of medical instruments, in particular to a degradable biomedical magnesium alloy, a vascular stent and preparation method therefor.

BACKGROUND OF THE INVENTION

The use process of the magnesium alloy vascular stent is a large deformation process. The stent needs to be pressed and held on the balloon delivery system firstly, and is inflated and expanded after reaching the lesion part, and the local strain can reach more than 15%. The vast majority of the surface treatments can cause localized breakage after stent expansion. For example, insoluble magnesium salts such as magnesium fluoride, magnesium carbonate, magnesium phosphate and hydroxyapatite or magnesium oxide, magnesium hydroxide and the like are used as the surface corrosion-resistant layer. Even if a high-firmness and dense surface corrosion-resistant layer is obtained by means of micro-arc oxidation, physical deposition, chemical conversion, electrochemical deposition and the like, due to the fact that a substance of the corrosion-resistant layer is brittle, damage or tiny cracks inevitably occur in a large deformation process, resulting in a loss of local protection effect. However, the broken or smooth fracture is a severe stress corrosion area, which will cause the supporting force of the stent to drop rapidly.

Another method for improving the corrosion resistance of the stent is to add a polymer coating on the surface of the magnesium alloy stent, considering the characteristics of the large deformation process of the stent, the polymer material with low elongation or low bonding firmness with the matrix cannot meet the actual requirements. In addition, due to the small size and complex structure of the stent, it is usually necessary to dissolve a polymer material in an organic solvent and then coat the surface of the stent by spraying or spin coating, and a protective coating is formed by volatilizing the organic solvent. The volatilization process of the organic solvent forms a tiny pore channel in the coating, and the magnesium alloy substrate may undergo an ion exchange with an external corrosion environment through the channel, thereby reducing the protective effect of the coating. Especially after a large deformation process, the corrosion of stress concentration is more obvious.

In addition, rapid degradation of the stent also leads to excessive local magnesium ion concentration to cause inflammation and proliferation. At present, vascular stent drugs and release systems thereof are generally designed for non-degradable stents or degradable stents that degrade particularly slowly (for example, polylactic acid substrates, pure iron substrates, etc.), and they are not suitable for magnesium alloy vascular stents that degrade rapidly.

SUMMARY OF THE INVENTION

An object of the present invention is to provide a degradable biomedical magnesium alloy.

Another object of the present invention is to provide a degradable biomedical magnesium alloy drug-eluting vascular stent.

Another object of the present invention is to provide a preparation method of the degradable biomedical magnesium alloy drug-eluting vascular stent.

After the vascular stent disclosed by the present invention undergoes a large deformation process under a near physiological condition, the composite coating still has a good protective effect on a stress concentration area, and inflammation and proliferation of an implanted part are inhibited through a unique composite drug controlled release system.

In order to achieve the above object, in one aspect, the present invention provides a degradable biomedical magnesium alloy, wherein the magnesium alloy comprises the following components in percentage by weight: 3.0-6.0% of Gd, 2.5-5.5% of Y, 1.0-3.0% of Li, 0.3-1.0% of Zn, 0.2-1.0% of Zr and balance of Mg, with regard to a total weight of the magnesium alloy of 100%.

According to some specific embodiments of the present invention, the magnesium alloy has a tensile strength of 260-350 MPa, a yield strength of 160-280 MPa, and an elongation at break of 10-28%.

The magnesium alloy has good biocompatibility and corrosion uniformity.

In another aspect, the present invention further provides a degradable biomedical magnesium alloy drug-eluting vascular stent, comprising a stent substrate 1, and a polymer intermediate layer 7, a polymer protective layer 6, and a drug coating layer 8 arranged from inside to outside of the stent substrate, wherein the stent substrate 1 comprises the following components in percentage by weight: 3.0-6.0% of Gd, 2.5-5.5% of Y, 0.3-1.0% of Zn, 0.2-1.0% of Zr and balance of Mg, with regard to a total weight of the stent substrate of 100%.

According to some specific embodiments of the present invention, the stent substrate 1, as shown in FIGS. 1 to 4, is mainly composed of a plurality of annular supports 2, a connector 3 and an end radiopaque marker structure 4; each support 2 and the radiopaque marker structure 4 are connected by the connector 3.

According to some specific embodiments of the present invention, any two adjacent supports 2 are mirror symmetric to each other.

According to some specific embodiments of the present invention, the support 2 is mainly composed of support units 5; each support unit 5 is composed of a wave rod 51, two wave rod connecting sections 52 and a circular arc body 53; the wave rod connecting sections 52 are arranged at two ends of the wave rod 51, wherein the wave rod connecting section 52 at one end is connected with one end of the two ends of the circular arc body 53 of the same support unit, and the wave rod connecting section 52 at the other end is connected with one end of the circular arc body 53 of the adjacent support unit (the other end of the circular arc body 53 of the same support unit is connected with the wave rod connecting section 52 of the other support unit 5, that is, the support units are connected end to end), thereby forming an annular support 2.

According to some specific embodiments of the present invention, the support 2 is mainly composed of 4-18 support units 5.

According to some specific embodiments of the present invention, the width of the wave rod 51 is 0.1 mm-0.18 mm.

According to some specific embodiments of the present invention, the length of the wave rod 51 is 0.35 mm-1.2 mm.

According to some specific embodiments of the present invention, the length of the wave rod 51 is 0.80 mm-1.2 mm.

According to some specific embodiments of the present invention, the width of the wave rod connecting section 52 is 0.01 mm-0.05 mm smaller than the width of the wave rod 51.

According to some specific embodiments of the present invention, the circular arc body 53 comprises an outer circular arc 531 on an outer side and an inner circular arc 532 on an inner side; both the centers of circles in which the inner circular arc 532 and the outer circular arc 531 are located on symmetry axes of two wave rods 51 connected to the same circular arc body 53, and are not concentric; a center of the outer circular arc 531 is located on a side of the center of the inner circular arc 532 facing a vertex of the circular arc; and the distance between the inner circular arc 532 and the outer circular arc 531 is smallest at a joint with the wave rod connecting section 52, and gradually increases toward the vertex of the circular arc body 53 until the symmetry axis is largest.

According to some specific embodiments of the present invention, the outer circular arc 531 has a diameter of 0.24-0.82 mm and a central angle of $\pi/2$-$3\pi/2$; the inner circular arc 532 has a diameter of 0.02-0.60 mm and a central angle of $\pi/2$-$3\pi/2$; and the distance between centers of the outer circular arc and the inner circular arc is 0.01-0.05 mm.

According to some specific embodiments of the present invention, the outer circular arc 531 has a diameter of 0.40-0.80 mm and a central angle of $\pi/2$-$3\pi/2$; the inner circular arc 532 has a diameter of 0.20-0.45 mm and a central angle of $\pi/2$-$3\pi/2$; and the distance between centers of the outer circular arc and the inner circular arc is 0.01-0.05 mm.

According to some specific embodiments of the present invention, the diameter of the outer circular arc 531 is larger than the diameter of the inner circular arc 532.

According to some specific embodiments of the present invention, the maximum distance between the inner circular arc 532 and the outer circular arc 531 (that is, the distance between the inner circular arc 532 and the outer circular arc 531 at the symmetry axis) is 0.01 mm-0.05 mm larger than the width of the wave rod, and the minimum distance (that is, the distance between the inner circular arc 532 and the outer circular arc 531 at two ends of the circular arc body 53) is 0.01-0.05 mm smaller than the width of the wave rod 51.

According to some specific embodiments of the present invention, the widths of the two ends of the wave rod connecting section 52 are respectively the same as the width of the wave rod 51 and the width of the end of the circular arc body 53 (that is, the width of the joint of the wave rod connecting section 52 and the wave rod 51 is the same as the width of the wave rod 51, and the width of the joint of the wave rod connecting section 52 and the circular arc body 53 is the same as the width of the end of the circular arc body 53, such that the wave rod connecting section 52 is in smooth transition connection with the wave rod 51 and the circular arc body 53), and the intermediate width is gradual transition (that is, the width of the wave rod gradually decreases from the joint with the wave rod 51 to the joint with the circular arc body 53).

According to the stent structure provided by the present invention, with the design of the unique non-concentric arc supporting unit 5, the stress distribution of the overall structure of the stent is uniform; and the stent structure is not easy to break in the process of severe deformation such as pressing, expansion and the like, the stress corrosion is relieved, and the service time of the stent is prolonged.

According to some specific embodiments of the present invention, the connector 3 has a shape of Type "C", "I" or "S".

According to some specific embodiments of the present invention, the radiopaque marker structure is provided at both ends of the stent substrate.

According to some specific embodiments of the present invention, the radiopaque marker structure comprises a radiopaque marker point 41 and a radiopaque marker structure body 42; the radiopaque marker structure body 42 is provided with a radiopaque marker hole 43.

According to some specific embodiments of the present invention, the radiopaque marker point 41 has a diameter of 0.2 mm-0.5 mm and a thickness of 0.1 mm-0.2 mm.

According to some specific embodiments of the present invention, the diameter of the radiopaque marker point 41 is 0.005 mm-0.01 mm smaller than the diameter of the radiopaque marker hole 43.

According to some specific embodiments of the present invention, one or two radiopaque marker holes 43 are provided on each radiopaque marker structure 4.

In order to avoid the interference of the observation angle of the stent development, the stent development holes are generally not in the same axis.

According to some specific embodiments of the present invention, the material of the radiopaque marker point 41 is selected from one or more of Pt, Au and Pt/Ir alloys.

According to some specific embodiments of the present invention, the radiopaque marker structure 4 is provided between the outermost two supports of the ends of the stent substrate (for example, between the first and second supports of the left end).

According to some specific embodiments of the present invention, the connector 3 between two adjacent supports connected to the radiopaque marker structure 4 is an "I" type structure, and the connector 3 between any other two adjacent supports is a "C" type structure.

According to some specific embodiments of the present invention, the radiopaque marker structure 4 is connected to the first support 2 (that is, the outermost support) at the end by a trapezoidal connector 44; and the radiopaque marker structure 4 is connected to the second support 2 at the end by an "I" type connector 45.

According to some specific embodiments of the present invention, the width of the two bottom edges of the trapezoidal connector 44 is 0.05-0.35 mm, and the width difference between the two bottom edges of the trapezoidal connector 44 is 0.02-0.08 mm.

According to some specific embodiments of the present invention, a long side (that is, a long bottom side) of the trapezoidal connector 44 is connected to the support 2, and a short side (that is, a short bottom side) of the trapezoidal connector 44 is connected to the radiopaque marker structure 4.

According to some specific embodiments of the present invention, the "I" type connector has a width of 0.05-0.18 mm.

The "I" connector body has a rectangular shape and forms a natural chamfer at the junction with the radiopaque marker structure and the supporting body.

According to some specific embodiments of the present invention, the stent has a crimping diameter of 0.8 mm-2.8 mm, an expansion diameter of 2.0 mm-8.0 mm, and a length of 6 mm-150 mm.

According to some specific embodiments of the present invention, the stent has a crimping diameter of 1.0 mm-2.0 mm, an expansion diameter of 2.2 mm-5.0 mm, and a length of 10 mm-50 mm.

According to some specific embodiments of the present invention, the stent has a crimping diameter of 1.0 mm-1.5 mm, an expansion diameter of 2.5 mm-3.5 mm, and a length of 10 mm-20 mm.

According to some specific embodiments of the present invention, the vascular stent further comprises a polymer protective layer 6 provided on a surface of the stent substrate 1, as shown in FIG. 5; the polymer of the polymer protective layer is polyvinylidene fluoride and a copolymer thereof (polyvinylidene fluoride-hexafluoropropylene copolymer); and the polymer protective layer 6 has a thickness of 2 μm-10 μm.

According to some specific embodiments of the present invention, the polymer protective layer 6 has a thickness of 4 μm-8 μm.

According to some specific embodiments of the present invention, the polymer protective layer 6 has a thickness of 5 μm-6 μm.

According to some specific embodiments of the present invention, the polymer protective layer 6 is subjected to an annealing treatment to reduce porosity.

The polymer protective layer 6 has a good biocompatibility, the elongation of 100-300% can meet the requirement of large deformation of the stent, and the extremely low water absorption of 0.01-0.05% can effectively block the contact between the body fluid or blood entering through the tiny holes and breaks in the stent drug controlled release coating and the magnesium alloy substrate, reduce ion exchange, and improve the corrosion resistance of the magnesium alloy stent.

According to some specific embodiments of the present invention, the vascular stent further comprises a polymer intermediate layer 7 provided between the stent substrate 1 and the polymer protective layer 6, as shown in FIG. 5; the polymer of the polymer intermediate layer is selected from one or more of polyvinylidene fluoride and a copolymer thereof (polyvinylidene fluoride-hexafluoropropylene copolymer), polymethyl methacrylate, and polybutyl methacrylate; and the polymer intermediate layer has a thickness of 100 nm-2000 nm.

According to some specific embodiments of the present invention, the polymer intermediate layer has a thickness of 500 nm-1500 nm.

According to some specific embodiments of the present invention, the polymer intermediate layer has a thickness of 800 nm-1200 nm.

According to some specific embodiments of the present invention, the polymer intermediate layer has a thickness of 800 nm-1000 nm.

The polymer intermediate layer can serve as an adhesive to improve the firmness of the polymer protective layer, and can block body fluid or blood permeated into tiny pore channels or uncovered areas of the polymer protective layer.

According to some specific embodiments of the present invention, the polymer intermediate layer 7 is a polymer intermediate layer subjected to a magnesium fluoride hole sealing treatment.

The magnesium fluoride hole sealing treatment refers to fluorination treatment of a magnesium alloy stent coated with the polymer intermediate layer.

Through fluorination treatment, a magnesium fluoride barrier is formed in tiny holes or uncovered areas of a magnesium alloy stent substrate (magnesium alloy substrate) and the polymer intermediate layer, and the contact between the magnesium alloy stent substrate and body fluid or blood is further blocked, so as to reduce local corrosion.

According to some specific embodiments of the present invention, the vascular stent further comprises a drug coating layer 8 provided on the outer surface of the polymer protective layer 6, as shown in FIG. 5; the drug coating layer comprises a polymer carrier and an active drug; the active drug is a combination of tacrolimus and one selected from rapamycin and arsenic trioxide (that is, a combination of tacrolimus and rapamycin, or a combination of tacrolimus and arsenic trioxide).

According to some specific embodiments of the present invention, the polymer material of the polymer carrier is selected from one or more of polylactic acid, racemic polylactic acid, polyglycolic acid, polylactic acid glycolic acid, polycaprolactone, and PHBV.

According to some specific embodiments of the present invention, the weight ratio of the polymer carrier to the active drug is 2:1-10:1.

According to some specific embodiments of the present invention, the weight ratio of the polymer carrier to the active drug is 4:1-8:1.

According to some specific embodiments of the present invention, the weight ratio of the polymer carrier to the active drug is 5:1-7:1.

According to some specific embodiments of the present invention, the weight ratio of arsenic trioxide or rapamycin to tacrolimus is 1:2-4:1.

According to some specific embodiments of the present invention, the weight ratio of arsenic trioxide or rapamycin to tacrolimus is 1:1-3:1.

According to some specific embodiments of the present invention, in the drug coating layer 8, the content of arsenic trioxide or rapamycin is 2-20 μg/mm, and the content of tacrolimus is 1-25 μg/mm.

According to some specific embodiments of the present invention, in the drug coating layer 8, the content of arsenic trioxide or rapamycin is 5-15 μg/mm, and the content of tacrolimus is 1-6 μg/mm.

According to some specific embodiments of the present invention, in the drug coating layer 8, the content of arsenic trioxide or rapamycin is 5-10 μg/mm, and the content of tacrolimus is 2-5 μg/mm.

In yet another aspect, the present invention further provides a preparation method of the degradable biomedical magnesium alloy drug-eluting vascular stent, comprising the following steps:
(1) processing of the stent substrate 1;
(2) coating of the polymer intermediate layer 7;
(3) coating of the polymer protective layer 6;
(4) coating of the drug coating layer 8.

According to some specific embodiments of the present invention, the processing of the stent substrate in step (1) comprises the following steps:
(11) making the degradable biomedical magnesium alloy into a magnesium alloy tube by a material forming process;
(12) making the magnesium alloy tube into a cutting stent by a laser engraving process;
(13) removing cutting residues and oxide layer by an ultrasonic cleaning treatment;
(14) obtaining a magnesium alloy stent substrate with smooth and flat surface by an electrochemical polishing process.

According to some specific embodiments of the present invention, the material forming process in step (11) comprises: preparing a magnesium alloy ingot by vacuum semi-continuous casting according to the components and weight ratios of the degradable biomedical magnesium alloy, performing a solid solution treatment and extrusion forming to prepare a magnesium alloy rod, and then preparing a magnesium alloy tube by a tube-drawing forming process.

According to some specific embodiments of the present invention, the magnesium alloy tube has an outer diameter of 1.4-4.0 mm, a wall thickness of 0.08-0.30 mm, and a length of 0.5-2.0 m.

The size of the magnesium alloy tube can be adjusted according to the expansion outer diameter of the magnesium alloy stent and the requirements of laser engraving equipment.

According to some specific embodiments of the present invention, the ultrasonic cleaning in step (13) comprises: immersing the cutting stent in step (12) in a magnesium alloy stent cleaning solution, and performing ultrasonic treatment for 1-8 min to remove cutting residues and oxide layer attached to the surface formed by the laser engraving.

According to some specific embodiments of the present invention, the magnesium alloy stent cleaning solution is prepared from potassium dihydrogen phosphate, potassium fluoride, anhydrous ethanol and purified water.

According to some specific embodiments of the present invention, in the magnesium alloy stent cleaning solution, based on the unit volume of the magnesium alloy stent cleaning solution, the contents of the components are: 30-50 g/L of potassium dihydrogen phosphate, 15-25 g/L of potassium fluoride, and 150-250 ml/L of anhydrous ethanol; preferably, 40 g/L of potassium dihydrogen phosphate, 20 g/L of potassium fluoride, and 200 ml/L of anhydrous ethanol.

According to some specific embodiments of the present invention, the electrochemical polishing process in step (14) comprises: immersing the cleaned cutting stent into a magnesium alloy stent polishing solution for electrochemical polishing, wherein the polishing temperature is 18-60° C., the polishing current is 0.3-1.5 A, and the polishing time is 10-500 s.

According to some specific embodiments of the present invention, the magnesium alloy stent polishing solution is prepared from phosphoric acid, anhydrous ethanol and purified water in a volume ratio of (0.8-1.2):(0.8-1.2):(0.8-1.2); preferably 1:1:1.

According to some specific embodiments of the present invention, the coating of the polymer intermediate layer in step (2) comprises the following steps:
(21) coating a polymer intermediate layer on the surface of a stent substrate;
(22) subjecting the stent surface-coated with the polymer intermediate layer to a fluorination treatment.

According to some specific embodiments of the present invention, step (21) comprises forming a polymer intermediate layer on the surface of the stent substrate by an ultrasonic spraying process.

According to some specific embodiments of the present invention, the fluorination treatment comprises: immersing the stent substrate coated with the polymer intermediate layer into a fluorination treatment solution, and performing a fluorination hole sealing treatment on the polymer intermediate layer.

According to some specific embodiments of the present invention, the fluorination treatment comprises: immersing the stent substrate coated with the polymer intermediate layer in a fluorination treatment solution, continuously stirring in a shaking bath at a rotation speed of 50-200 r/min, and performing a fluorination hole sealing treatment on the polymer intermediate layer.

According to some specific embodiments of the present invention, the fluorination treatment solution is prepared from a hydrofluoric acid solution and a potassium fluoride solution.

According to some specific embodiments of the present invention, the concentration of the hydrofluoric acid solution is 10-40% (volume concentration); the concentration of the potassium fluoride solution is 0.5-5 mol/L; and the volume ratio of the hydrofluoric acid solution to the potassium fluoride solution is 100:5-100:50.

According to some specific embodiments of the present invention, the temperature of the fluorination treatment solution is 18-85° C., and the treatment time is 30-600 min.

According to some specific embodiments of the present invention, the coating of the polymer protective layer in step (3) comprises the following steps:
(31) coating a polymeric protective layer;
(32) subjecting the coated polymer protective stent to an annealing treatment.

According to some specific embodiments of the present invention, step (31) comprises forming a polymer protective layer on the surface of the fluorinated polymer intermediate layer by an ultrasonic spraying process.

According to some specific embodiments of the present invention, wherein the annealing treatment in step (32) comprises: heating the stent coated with the polymer protective layer to 60-200° C. for 1-10 h under a vacuum condition, and taking out the stent after cooling to room temperature.

According to some specific embodiments of the present invention, the temperature of the annealing treatment is 100-150° C.; preferably, 120-130° C.

According to some specific embodiments of the present invention, the time of the annealing treatment is 2-8 h.

According to some specific embodiments of the present invention, the annealing treatment comprises: placing the stent coated with the polymer protective layer into a quartz dish for annealing treatment.

According to some specific embodiments of the present invention, the vacuum degree of the vacuum condition is greater than or equal to $1 \times 10^{-3}$ Pa.

According to some specific embodiments of the present invention, the annealing treatment comprises: after naturally cooling to below 50° C., introducing argon gas, continually cooling down to room temperature, and taking out the stent.

According to some specific embodiments of the present invention, step (4) comprises forming a drug coating layer on the surface of the stent protective coating by an ultrasonic spraying process.

According to some specific embodiments of the present invention, the ultrasonic spraying process in steps (21), (31) and (4) refers to: dissolving raw materials (polymers, or a mixture of a polymer carrier and an active drug) of each layer to be sprayed in each step in a volatile organic solvent, and spraying them on the surface of the stent or the adjacent inner layer (polymer intermediate layer or polymer protective layer) after ultrasonic atomization, whereby the organic solvent volatilizes to form a corresponding layer structure (polymer intermediate layer, polymer protective layer or drug coating layer).

According to some specific embodiments of the present invention, the method comprises the following steps:
(a) making the degradable biomedical magnesium alloy into a magnesium alloy tube by a material forming process;
(b) making the magnesium alloy tube into a cutting stent by a laser engraving process;
(c) removing cutting residues and oxide layer by an ultrasonic cleaning treatment;
(d) obtaining a magnesium alloy stent substrate with smooth and flat surface by an electrochemical polishing process;
(e) forming a polymer intermediate layer on the surface of the magnesium alloy stent substrate by an ultrasonic spraying process;
(f) treating the magnesium alloy stent surface-coated with the polymer intermediate layer by a fluorination treatment process;

(g) forming a polymer protective layer on the surface of the fluorinated polymer intermediate layer by an ultrasonic spraying process;

(h) sealing holes in the stent protective coating layer by an annealing treatment;

(i) forming a drug coating layer on the surface of the stent protective coating layer by an ultrasonic spraying process; and (j) drying to obtain the degradable biomedical magnesium alloy drug-eluting vascular stent.

In yet another aspect, the present invention further provides an application of the degradable biomedical magnesium alloy drug-eluting vascular stent in the preparation of a medical device for treating vascular stenosis.

In yet another aspect, the present invention further provides an application of the degradable biomedical magnesium alloy drug-eluting vascular stent in the preparation of a medical device for treating vascular stenosis.

In yet another aspect, the present invention further provides a method for evaluating a degradable biomedical magnesium alloy drug-eluting vascular stent in an animal model of vascular stenosis, comprising: firstly, subjecting the animal model to a pretreatment; after forming a vascular embolization model, implanting the degradable biomedical magnesium alloy drug-eluting vascular stent provided by the present invention; performing follow-up visits at different postoperative times, wherein the follow-up visits are angiography observation and intravascular OCT observation, for evaluating the intimal coverage degree, restenosis and degradation of the stent.

According to some specific embodiments of the present invention, the pretreatment of the animal model refers to performing blood vessel dilation by using a disposable balloon dilation catheter at the blood vessel position where the stent is expected to be implanted, wherein the dilation ratio is 1.3-1.5 times of the diameter of the blood vessel. This causes damage to the blood vessel to a certain extent and a model of vascular stenosis can develop 1-4 weeks after the pretreatment.

According to some specific embodiments of the present invention, implantation refers to implanting the degradable biomedical magnesium alloy drug-eluting vascular stent provided by the present invention into a stenosis model, wherein the stent expansion ratio is 1.1-1.3 times of the diameter of the blood vessel.

In summary, the present invention provides a degradable biomedical magnesium alloy drug-eluting vascular stent and a preparation method thereof. The vascular stent of the present invention has the following advantages:

The substrate material of the vascular stent provided by the present invention is a medical magnesium alloy material which can be absorbed by a human body, and has excellent properties of high tensile strength, high elongation, high corrosion resistance, uniform degradation and the like.

The structural design of the vascular stent provided by the present invention can effectively reduce the stress concentration degree during stent expansion, and can be developed under X-ray.

After the polymer of the vascular stent provided by the present invention is subjected to the magnesium fluoride hole sealing treatment, a magnesium fluoride barrier can be formed at tiny holes or an uncovered area of a stent coating, such that contact between a stent substrate and body fluid or blood is further blocked, and the local corrosion is effectively reduced.

The polymer protective layer of the vascular stent provided by the present invention has extremely high hydrophobicity, can effectively block ion exchange between the stent and body fluid or blood, and improves the corrosion resistance of the stent.

The protective layer annealing treatment method for the vascular stent provided by the present invention can effectively reduce the porosity, improve the binding force with the substrate, reduce the damage of the protective layer during large deformation of the stent, and further improve the corrosion resistance of the stent.

The vascular stent composite drug coating layer provided by the present invention utilizes the characteristics that arsenic trioxide or rapamycin drugs inhibit growth of smooth muscle cells and promote growth of endothelial cells, resulting in rapid endothelialization, and the thrombus risk and the stent degradation shedding risk are effectively reduced; and by utilizing the good anti-inflammatory effect of tacrolimus drugs, the inflammatory reaction generated in the stent degradation process is effectively inhibited, and proliferation and intra stent restenosis are reduced.

The vascular stent provided by the present invention shows a good treatment result in a large animal experiment for simulating coronary artery stenosis. The blood vessel lumen has no collapse, no inflammation and no intimal hyperplasia in a 6-month follow-up visit. Adequate safety and efficacy were demonstrated in the degradation process.

DETAILED DESCRIPTION OF THE INVENTION

Figure 1:
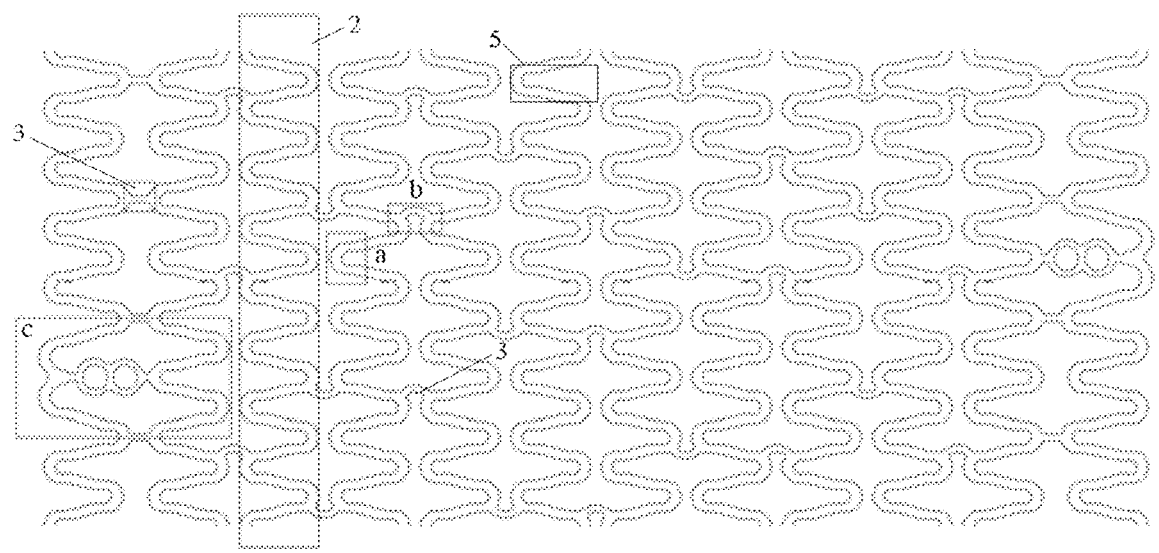
FIG. 1 is an overall schematic diagram of a structure of the degradable biomedical magnesium alloy drug-eluting vascular stent of the present invention.
Figure 2:
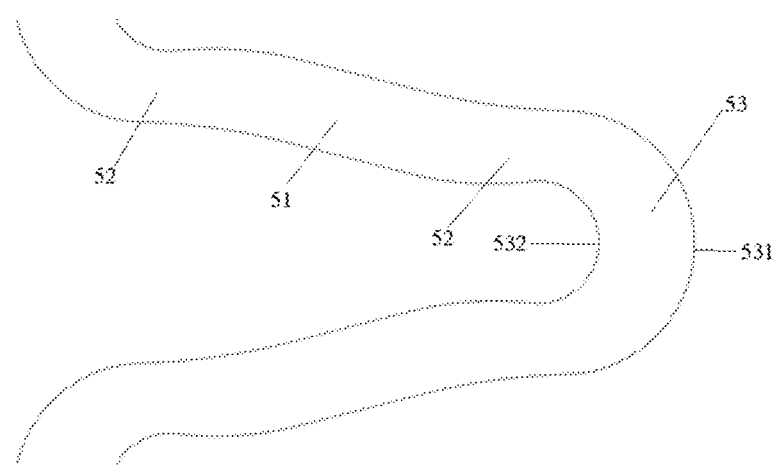
FIG. 2 is an enlarged view of Part a of FIG. 1.
Figure 3:
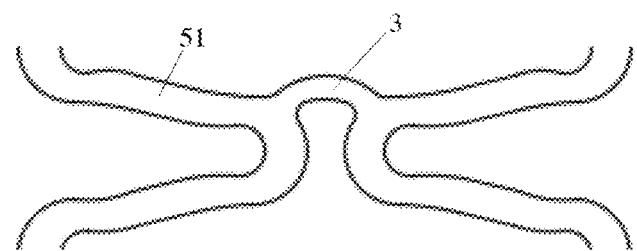
FIG. 3 is an enlarged view of Part b of FIG. 1.
Figure 4:
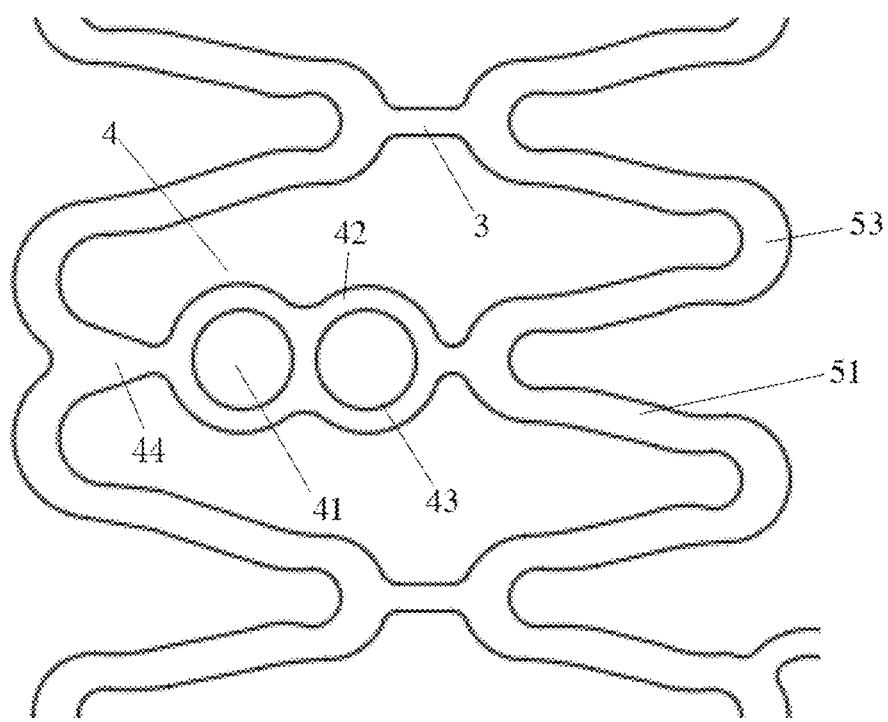
FIG. 4 is an enlarged view of Part c of FIG. 1.
Figure 5:
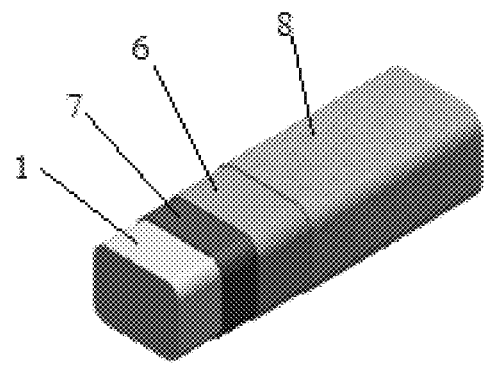
FIG. 5 is a schematic diagram of a composite coating of the degradable biomedical magnesium alloy drug-eluting vascular stent of the present invention.

The technical solutions of the present invention are described in detail below with reference to the accompanying drawings and examples, but the protection scope of the present invention comprises but is not limited thereto.

Magnesium Alloy Material Example 1

This example provides a series of degradable biomedical magnesium alloy materials, and the elemental component contents thereof are shown in Table 1:

TABLE 1

Element contents of degradable biomedical magnesium alloy materials

| Material No. | Gd(wt %) | Y(wt %) | Li(wt %) | Zn(wt %) | Zr(wt %) | Balance |
|---|---|---|---|---|---|---|
| BDM-6# | 3.6 | 2.6 | 1.2 | 0.6 | 0.5 | Mg |
| BDM-7# | 4.5 | 3.5 | 1.5 | 0.7 | 0.5 | Mg |
| BDM-8# | 5.0 | 4.2 | 1.5 | 0.8 | 0.5 | Mg |
| BDM-9# | 6.0 | 5.5 | 2.5 | 0.9 | 1.0 | Mg |
| BDM-10# | 3.0 | 2.5 | 1.0 | 0.3 | 0.2 | Mg |

The processing method comprises the following steps: Alloy elements were smelt into a magnesium alloy ingot by using a vacuum semi-continuous casting mode according to the content ratio of all the elements in Table 1, wherein the purity of each of the raw materials was 99.99%. The magnesium alloy ingot was subjected to solution treatment at a solution temperature of 450° C. for 8 h, and then the magnesium alloy ingot was extruded into a rod with a diameter of 10 mm by hot extrusion at 340° C. 20% of the length of each end of the rod are cut off, and only the middle section of the rod is used as a preparation material of the vascular stent, so as to avoid the influence of uneven mixing.

Stent Structure Example 1

This example provides a group of magnesium alloy vascular stent structures, which are made of the BDM-6 #material in the Magnesium Alloy Material Example 1, and are composed of stent substrates 1 with different parameters. The structural parameters of different groups are shown in Table 2, wherein the control group is an example of the magnesium alloy stent structure described in Patent CN201520261612.

TABLE 2

Comparison of stent structures with different parameters.

| Structural parameters | Control group | Structure A | Structure B | Structure C | Structure D |
|---|---|---|---|---|---|
| Width of the wave rod/mm | 0.12 | 0.12 | 0.10 | 0.12 | 0.18 |
| Wave rod length/mm | 0.80 | 0.80 | 0.80 | 1.00 | 1.20 |
| Wave rod connecting section width/mm | 0.12 | 0.10 | 0.08 | 0.10 | 0.15 |
| Outer circular arc diameter/mm | 0.42 | 0.44 | 0.40 | 0.44 | 0.80 |
| Outer circular arc central angle | $\pi/2$ | $\pi/2$ | $\pi/2$ | $\pi/2$ | $3\pi/2$ |
| Inner circular arc diameter/mm | 0.18 | 0.22 | 0.20 | 0.20 | 0.42 |
| Inner circular arc central angle | $\pi/2$ | $\pi/2$ | $\pi/2$ | $\pi/2$ | $3\pi/2$ |
| Center spacing between inner and outer circular arcs/mm | 0 | 0.03 | 0.02 | 0.02 | 0.05 |
| Stent wall thickness/mm | 0.14 | 0.14 | 0.10 | 0.12 | 0.14 |
| Support unit number | 6 | 6 | 8 | 6 | 4 |

In addition to the different parameters shown in Table 2, the remaining parameters of each group of structures are the same, that is, the stent substrate 1 further comprises a radiopaque marker structure 4 connected to two ends of the stent substrate through a connecting body 3; the radiopaque marker structure comprises a radiopaque marker point 41 made of platinum and a radiopaque marker structure body 42; and the radiopaque marker structure body 42 is provided with a radiopaque marker hole 43. The radiopaque marker point 41 has a diameter of 0.35 mm and a thickness of 0.14 mm; and the stent substrate 1 has a compressed diameter of 1.3 mm, an expanded diameter of 3.0 mm and a length of 13 mm.

Stent Example 1

This example provides a degradable biomedical magnesium alloy drug-eluting vascular stent (as shown in FIG. 1 to FIG. 5), which comprises a stent substrate 1, and a polymer intermediate layer 7, a polymer protective layer 6 and a drug coating layer 8 coated from inside to outside.

The stent substrate 1 adopts the structure A in the Stent Structure Example 1, and the material thereof is the BDM-6 #material in the Magnesium Alloy Material Example 1.

The polymer intermediate layer 7 is subjected to a magnesium fluoride hole sealing treatment, wherein the polymer is polyvinylidene fluoride with a thickness of 1000 nm.

The polymer of the polymer protective layer 6 is polyvinylidene fluoride-hexafluoropropylene with a thickness of 6 µm.

The drug coating layer comprises a polymer carrier and an active drug; the polymer material of the polymer carrier is PLLA; the active drug is arsenic trioxide and tacrolimus in a weight ratio of 1:1; and the weight ratio of the polymer carrier to the active drug is 5:1. The arsenic trioxide content is 5 µg/mm, and the tacrolimus content is 5 µg/mm.

The preparation of the degradable biomedical magnesium alloy drug-eluting vascular stent comprises the following steps:

(a) A BDM-6 #magnesium alloy rod was prepared by the Magnesium Alloy Material Example 1, and it was then subject to a tube-drawing molding process to produce a magnesium alloy tube. The magnesium alloy tube has an outer diameter of 3.0 mm, a wall thickness of 0.22 mm and a length of 1 m.

(b) The magnesium alloy tube was made into a cutting stent by a laser engraving process.

(c) The stent subjected to the laser engraving process was immersed in a magnesium alloy stent cleaning solution and subjected to an ultrasonic treatment for 2 min to remove cutting residues and an oxide layer attached to the surface formed by the laser engraving. The magnesium alloy stent cleaning solution was prepared from potassium dihydrogen phosphate, potassium fluoride, anhydrous ethanol and purified water, specifically 40 g/L of potassium dihydrogen phosphate, 20 g/L of potassium fluoride and 200 ml/L of anhydrous ethanol, and the solvent is purified water.

(d) The cleaned cutting stent was clamped by a clamp and immersed in a magnesium alloy stent polishing solution for electrochemical polishing, wherein the polishing temperature was 40° C., the polishing current was 1.2 A, and the polishing time was 80 s. The magnesium alloy stent polishing solution was prepared from phosphoric acid, anhydrous ethanol and purified water in a volume ratio of 1:1:1.

(e) A polymer intermediate layer was formed on the surface of the magnesium alloy stent substrate by an ultrasonic spraying process.

(f) The stent surface-coated with the polymer intermediate layer was immersed in a fluorination treatment solution, continuously stirred in a shaking bath at a rotation speed of 80 r/min, and the polymer primer was subjected to a fluorination hole sealing treatment. The fluorination treatment solution was prepared from a hydrofluoric acid solution and a potassium fluoride solution. Specifically, the concentration of the hydrofluoric acid solution was 40%, the concentration of the potassium fluoride solution was 5 mol/L, and the volume ratio of the hydrofluoric acid solution to the potassium fluoride solution was 100:30. The temperature of the fluorination treatment solution was 75° C., and the treatment time was 300 min.

(g) A polymer protective layer was formed on the surface of the fluorinated polymer intermediate layer by an ultrasonic spraying process.

(h) A stent coated with a polymer protective layer was vertically placed in a quartz tube, and vacuum pumping was started after being fed into a furnace. When the vacuum degree was higher than $1 \times 10^{-3}$ Pa, heating was started, and the temperature was kept at 120° C. for 2 h. As the furnace was cooled down to below 120° C., argon was introduced into the quartz tube, and the stent was taken out after the temperature was reduced to room temperature.

(i) A drug coating layer was formed on the surface of the stent protective coating layer by an ultrasonic spraying process.

(j) After drying, the degradable biomedical magnesium alloy drug-eluting vascular stent was produced.

Figure 28:
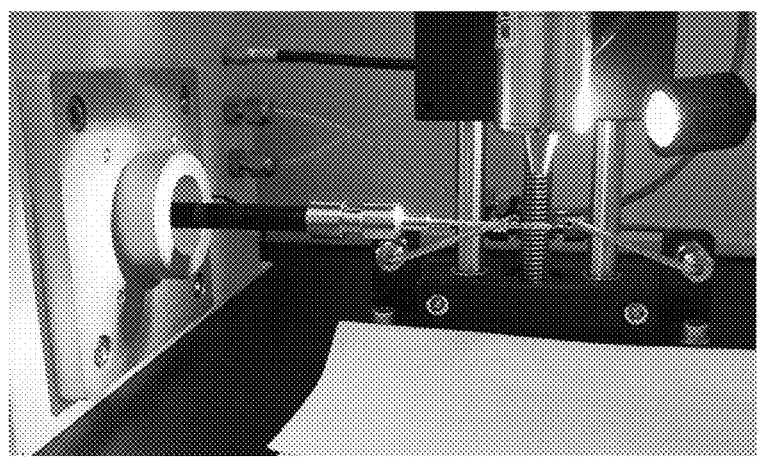
FIG. 28 is a photograph of the ultrasonic spraying process of Stent Example 4 of the present invention.

The ultrasonic spraying refers to covering the surface of the stent with a polymer by using an ultrasonic spraying machine. As shown in FIG. 28, the spraying height is 30 mm, the air pressure is 11 KPa, and the rotation speed is 205 r/min.

Stent Example 2

The present example provides a degradable biomedical magnesium alloy drug-eluting vascular stent, wherein a bare stent (no surface treatment and no coating) is only formed of the stent substrate 1.

The stent substrate 1 adopts a structure A with a relatively high radial supporting force and a relatively small maximum equivalent strain in the Stent Structure Example 1, and is made of a BDM-6 #material with a relatively good mechanical properties and corrosion resistance in the Magnesium Alloy Material Example 1.

(a) A BDM-6 #magnesium alloy rod was prepared by the Magnesium Alloy Material Example 1, and it was then subject to a tube-drawing molding process to produce a magnesium alloy tube. The magnesium alloy tube has an outer diameter of 3.0 mm, a wall thickness of 0.22 mm and a length of 1 m.

(b) The magnesium alloy tube was made into a cutting stent by a laser engraving process.

(c) The stent subjected to the laser engraving process was immersed in a magnesium alloy stent cleaning solution and subjected to an ultrasonic treatment for 2 min to remove cutting residues and an oxide layer attached to the surface formed by the laser engraving. The magnesium alloy stent cleaning solution was prepared from potassium dihydrogen phosphate, potassium fluoride, anhydrous ethanol and purified water, specifically 40 g/L of potassium dihydrogen phosphate, 20 g/L of potassium fluoride and 200 ml/L of anhydrous ethanol, and the solvent is purified water.

(d) The cleaned cutting stent was clamped by a clamp and immersed in a magnesium alloy stent polishing solution for electrochemical polishing, wherein the polishing temperature was 40° C., the polishing current was 1.2 A, and the polishing time was 80 s. The magnesium alloy stent polishing solution was prepared from phosphoric acid, anhydrous ethanol and purified water in a volume ratio of 1:1:1.

(e) After cleaning and drying, the degradable biomedical magnesium alloy drug-eluting vascular stent was produced.

Stent Example 3

This example provides a degradable biomedical magnesium alloy drug-eluting vascular stent, which comprises a stent substrate 1 and a magnesium fluoride protective layer.

The stent substrate 1 adopts a structure A with a relatively high radial supporting force and a relatively small maximum equivalent strain in the Stent Structure Example 1, and is made of a BDM-6 #material with a relatively good mechanical properties and corrosion resistance in the Magnesium Alloy Material Example 1.

The magnesium fluoride protective layer is composed of dense magnesium fluoride and uniformly covers the surface of the stent with a thickness of 1000 nm.

(a) A BDM-6 #magnesium alloy rod was prepared by the Magnesium Alloy Material Example 1, and it was then subject to a tube-drawing molding process to produce a magnesium alloy tube. The magnesium alloy tube has an outer diameter of 3.0 mm, a wall thickness of 0.22 mm and a length of 1 m.

(b) The magnesium alloy tube was made into a cutting stent by a laser engraving process.

(c) The stent subjected to the laser engraving process was immersed in a magnesium alloy stent cleaning solution and subjected to an ultrasonic treatment for 2 min to remove cutting residues and an oxide layer attached to the surface formed by the laser engraving. The magnesium alloy stent cleaning solution was prepared from potassium dihydrogen phosphate, potassium fluoride, anhydrous ethanol and purified water, specifically 40 g/L of potassium dihydrogen phosphate, 20 g/L of potassium fluoride and 200 ml/L of anhydrous ethanol, and the solvent is purified water.

(d) The cleaned cutting stent was clamped by a clamp and immersed in a magnesium alloy stent polishing solution for electrochemical polishing, wherein the polishing temperature was 40° C., the polishing current was 1.2 A, and the polishing time was 80 s. The magnesium alloy stent polishing solution was prepared from phosphoric acid, anhydrous ethanol and purified water in a volume ratio of 1:1:1.

(e) The stent substrate or stent substrate unit was immersed in a fluorination treatment solution, continuously stirred in a shaking bath at a rotation speed of 80 r/min, and subjected to fluorination treatment. The fluorination treatment solution was prepared from a hydrofluoric acid solution and a potassium fluoride solution. Specifically, the concentration of the hydrofluoric acid solution was 40%, the concentration of the potassium fluoride solution was 5 mol/L, and the volume ratio of the hydrofluoric acid solution to the potassium fluoride solution was 100:30. The temperature of the fluorination treatment solution was 75° C., and the treatment time was 300 min.

(f) After cleaning and drying, the degradable biomedical magnesium alloy drug-eluting vascular stent was produced.

Stent Example 4

This example provides a degradable biomedical magnesium alloy drug-eluting vascular stent, which comprises a stent substrate 1, a magnesium fluoride intermediate layer, and a polymer protective layer.

The stent substrate 1 adopts a structure A with a relatively high radial supporting force and a relatively small maximum equivalent strain in the Stent Structure Example 1, and is made of a BDM-6 #material with a relatively good mechanical properties and corrosion resistance in the Magnesium Alloy Material Example 1.

The magnesium fluoride intermediate layer is composed of dense magnesium fluoride and uniformly covers the surface of the stent with a thickness of 1000 nm.

The polymer of the polymer protective layer is polymethyl methacrylate with a thickness of 6 μm.

(a) A BDM-6 #magnesium alloy rod was prepared by the Magnesium Alloy Material Example 1, and it was then subject to a tube-drawing molding process to produce a magnesium alloy tube. The magnesium alloy tube has an outer diameter of 3.0 mm, a wall thickness of 0.22 mm and a length of 1 m.

(b) The magnesium alloy tube was made into a cutting stent by a laser engraving process.

(c) The stent subjected to the laser engraving process was immersed in a magnesium alloy stent cleaning solution and subjected to an ultrasonic treatment for 2 min to remove cutting residues and an oxide layer attached to the surface formed by the laser engraving. The magnesium alloy stent cleaning solution was prepared from potassium dihydrogen phosphate, potassium fluoride, anhydrous ethanol and purified water, specifically 40 g/L of potassium dihydrogen phosphate, 20 g/L of potassium fluoride and 200 ml/L of anhydrous ethanol, and the solvent is purified water.

(d) The cleaned cutting stent was clamped by a clamp and immersed in a magnesium alloy stent polishing solution for electrochemical polishing, wherein the polishing temperature was 40° C., the polishing current was 1.2 A, and the polishing time was 80 s. The magnesium alloy stent polishing solution was prepared from phosphoric acid, anhydrous ethanol and purified water in a volume ratio of 1:1:1.

(e) The stent substrate or stent substrate unit was immersed in a fluorination treatment solution, continuously stirred in a shaking bath at a rotation speed of 80 r/min, and subjected to fluorination treatment. The fluorination treatment solution was prepared from a hydrofluoric acid solution and a potassium fluoride solution. Specifically, the concentration of the hydrofluoric acid solution was 40%, the concentration of the potassium fluoride solution was 5 mol/L, and the volume ratio of the hydrofluoric acid solution to the potassium fluoride solution was 100:30. The temperature of the fluorination treatment solution was 75° C., and the treatment time was 300 min.

(f) A polymethyl methacrylate protective layer is formed on the surface of the magnesium fluoride protective layer by an ultrasonic spraying process.

(j) After cleaning and drying, the degradable biomedical magnesium alloy drug-eluting vascular stent was produced.

The ultrasonic spraying refers to covering the surface of the stent with a polymer by using an ultrasonic spraying machine, wherein the spraying height is 30 mm, the air pressure is 11 KPa, and the rotating speed is 205 r/min.

Test Example 1

Evaluation of mechanical properties and degradation performance of the degradable biomedical magnesium alloy material Testing material: The material of Magnesium Alloy Material Example 1.

Testing method: Mechanical properties were tested according to the test method described in "GB/T228.1-2010 metal material tensile test, Part 1: Room temperature test method". Cytotoxicity testing was performed using co-culture.

Description of Results:

The medical magnesium alloy material provided by the present invention can show different mechanical properties and corrosion resistance under different alloy element component conditions. The proportion of alloy elements may be adjusted according to different implantation requirements of different medical instruments, so as to control the degradation rate and mechanical properties of the substrate material. Preferably, the magnesium alloy substrate material suitable for the vascular stent needs high corrosion resistance, and the mechanical properties can be remarkably improved at the application end through the structure design of the degradable vascular stent provided by the present invention.

Figure 6:
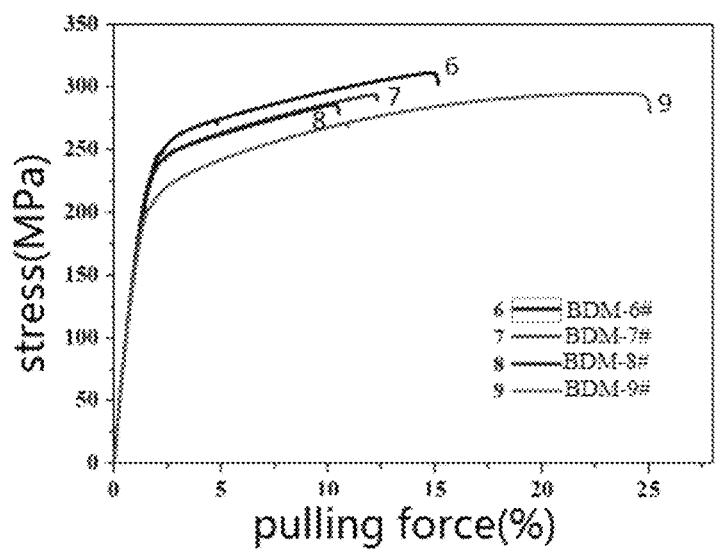
FIG. 6 is a drawing curve of Test Example 1 of the present invention.
Figure 7:
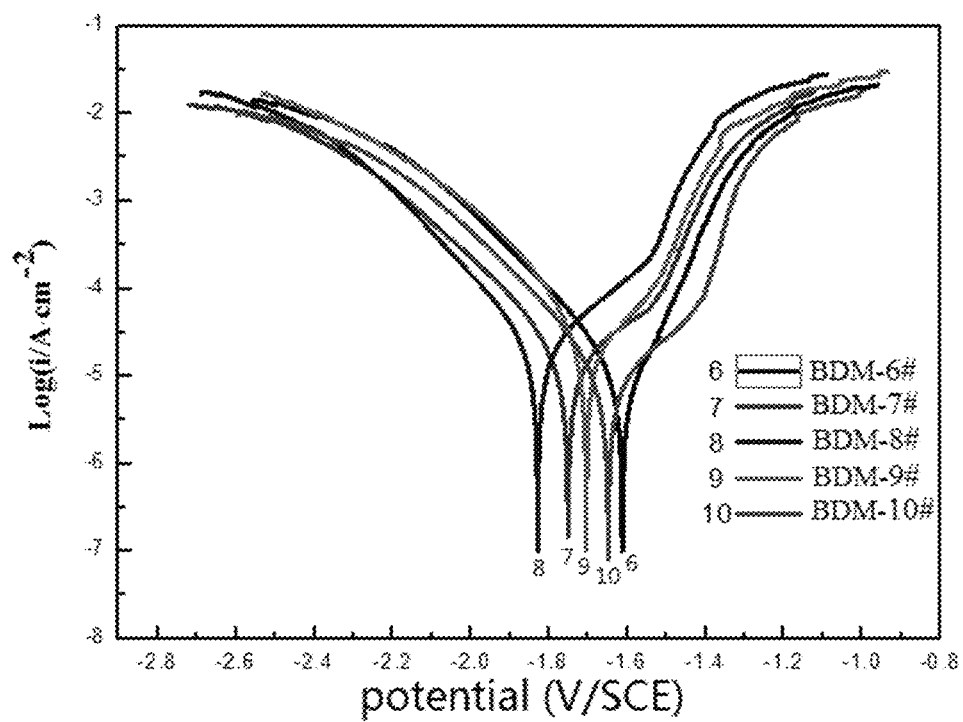
FIG. 7 is a corrosion potential diagram of Test Example 1 of the present invention.

The drawing curve is shown in FIG. 6, the corrosion potential is shown in FIG. 7, and mechanical properties such as tensile strength are shown in Table 3 below.

TABLE 3

| | Mechanical properties of the degradable biomedical magnesium alloy | | |
|---|---|---|---|
| Samples | Tensile strength (MPa) | Yield strength (MPa) | Elongation at Break (%) |
| BDM-6# | 311 | 249 | 15 |
| BDM-7# | 294 | 238 | 12 |
| BDM-8# | 286 | 238 | 10 |
| BDM-9# | 295 | 200 | 25 |
| BDM-10# | 285 | 236 | 11 |

In addition, when a co-culture method was used to test the cytotoxicity of the magnesium alloy materials, the relative value-added rate of the materials all reached more than 90%, and the cytotoxicity was grade 1, which satisfies the characteristics of biomaterials. The results are shown in Table 4.

TABLE 4

Cytotoxicity test results

| Material grouping | Relative value-added rate/% | Cytotoxicity grade |
|---|---|---|
| Blank control | 102.67236813 | 0 |
| BDM-6# | 97.60985385 | 1 |
| BDM-7# | 95.22345721 | 1 |
| BDM-8# | 92.63721764 | 1 |
| BDM-9# | 94.36271836 | 1 |
| BDM-10# | 97.98375234 | 1 |
| Positive control | 38.63336529 | 4 |

Test Example 2

Stent Stress Finite Element Analysis Test

Testing Method:

(1) Modelling: Models were established in 1:1 according to the structural dimensions of each group of stent substrates 1 described in the Stent Structure Example 1.

(2) Material properties: Since the vascular stent was expanded into a large deformation process, real stress and plastic strain should be used in the nonlinear finite element analysis process, and the test stress and test strain obtained by the material tensile experiment have to be converted into real stress and plastic strain. The stress/strain data of the BDM-6 #material in Magnesium Alloy Material Example 1 was converted into data of real stress/plastic strain, which was assigned to the model. The conversion formula is as follows:

$$\sigma_{true} = \sigma_{nom}(1 + \varepsilon_{nom})$$

$$\varepsilon_{pl} = |\ln(1 + \varepsilon_{nom})| - \frac{|\sigma_{true}|}{E}$$

wherein, $\sigma_{true}$ is a true stress, $\varepsilon_{pi}$ is a plastic strain, $\sigma_{nom}$ is a testing stress, and $\varepsilon_{nom}$ is a testing strain.

(3) Grid division: Cell size of 0.016, division of 6 layers of grids in the thickness direction, and a 8-node hexahedron linear reduction integration unit C3D8R were selected. This unit is more accurate for displacement solutions. When the mesh has twisted deformation (e.g., the angle of the Quad cell is large, much larger than 900), the analysis accuracy will not be greatly affected, and shearing self-locking is not easy to occur under bending loads.

(4) The boundary condition: A columnar coordinate system was established at the end part of the central shaft of the model, axial constraint and circumferential constraint were applied to one end of the model, and axial rigid body displacement and end circumferential rotation displacement of the model were limited; radial expansion displacement was applied to the inner surface of the model, and radial crimping displacement was applied to the outer surface.

(5) The stress/strain distribution of the support structure was calculated, and the bearing reaction force was calculated to evaluate the radial supporting force of the support.

(6) The comparison results are shown in Table 5 below:

TABLE 5

Comparison of properties of stent structures with different parameters

| Stent structure | Control group | Structure A | Structure B | Structure C | Structure D |
|---|---|---|---|---|---|
| Maximum equivalent strain/% | 13.6 | 10.5 | 7.3 | 8.3 | 13.3 |
| Radial supporting force/kPa | 121 | 142 | 111 | 122 | 164 |

Description of Results:

The maximum equivalent strain represents the stress concentration when the stent is expanded, and the larger the value, the higher the stress concentration; and the closer the elongation at break of the material, the easier the fracture. As shown in Table 5, the maximum equivalent strain of the control has become close to the elongation at break (15%) of the material, and the risk of fracture is high, but the supporting force is only 121 kPa. Compared with the control group, the stent structure A provided by the present invention obviously reduces the maximum equivalent strain of the stent and greatly improves the radial supporting force level of the stent. Compared with the control group, the stent structure B provided by the present invention has lower maximum equivalent strain, and can provide higher expansion safety under the condition that the radial supporting force requirement is not high (such as small-scale cerebrovascular lesions). Compared with the control group, the stent structure C provided by the present invention has the advantages that the maximum equivalent strain is greatly reduced and the expansion safety of the stent is improved while keeping the radial supporting force close to that of the control group. Compared with the control group, the stent structure D provided by the present invention has the maximum equivalent strain close to that of the control group, and can provide higher radial supporting force under the condition of lower risk of stent fracture (such as subpatellar vascular lesions).

In the case of common vascular stents, for example, the patent CN201520261612 discloses an open loop tube mesh magnesium alloy vascular stent (control group), and the main support unit is in the form of "sinusoidal wave". Although the support units are also connected by C-shaped arcs, in the expanded state of the stent, a serious stress/strain concentration phenomenon exists on the inner side of each waveform arc of the "sinusoidal wave" main support unit.

Figure 8:
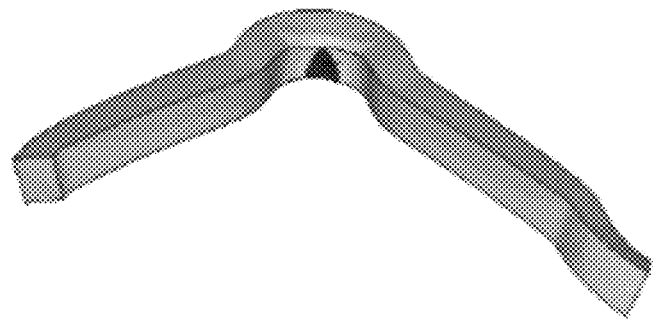
FIG. 8 is a stress diagram of a general vascular stent of Test Example 2 of the present invention.

By calculation, the structural stress concentration is at the center of the inner side of the peak, and the stent is easy to break during expansion, as shown in FIG. 8. Due to poor plasticity of the magnesium alloy, in the practical application process, a process of crimping (the outer diameter is about 1.0-1.2 mm) at first and then expanding (the outer diameter is 2.5-4.0 mm) is required, and serious stress concentration will cause expansion and fracture of the stent. In the structural parameter range described in this patent, the overall stress/strain of the stent after expansion can be reduced by increasing the waveform height, but the radial supporting force may be severely reduced. By reducing the size of the stent substrate, the overall stress/strain of the stent after expansion may also be reduced, and the thinner stent substrate increases the risk of corrosion and fracture while losing the radial supporting force, which is also not conducive to resisting fatigue damage.

The present application focuses on optimizing the stress concentration locations and the innovative circular arc design to homogenize the stress distribution, in order to ensure sufficient size to reduce the risk of structural damage due to degradation while retaining sufficient expansion safety desirability. The stress distribution diagrams measured by using the Stent Example 2 of the present application as a test sample are shown in FIGS. 9 and 10.

Figure 9:
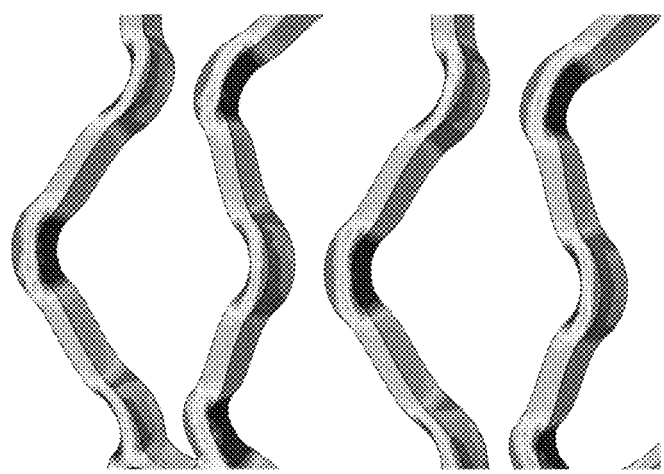
FIGS. 9 and 10 are stress diagrams of the degradable biomedical magnesium alloy drug-eluting vascular stent of Test Example 2 of the present invention.
Figure 10:
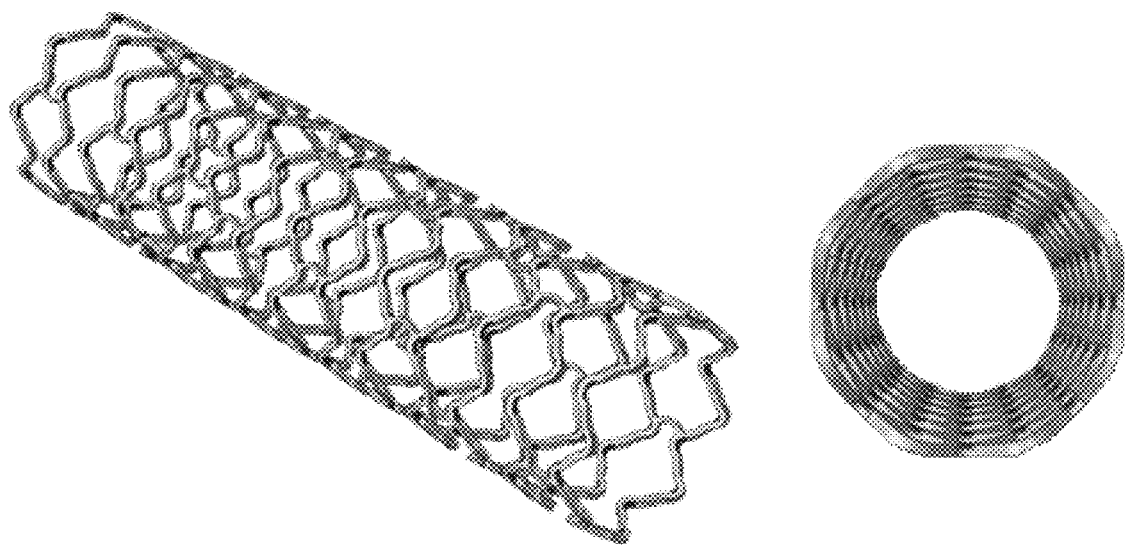

From FIG. 9 and FIG. 10, it can be seen that the stress/strain of the present application is uniformly distributed to the beams on both sides, and the stress/strain is uniformly distributed on the premise of ensuring that the beam width is unchanged, thereby greatly improving the safety performance of the magnesium alloy stent.

Test Example 3

Figure 11:
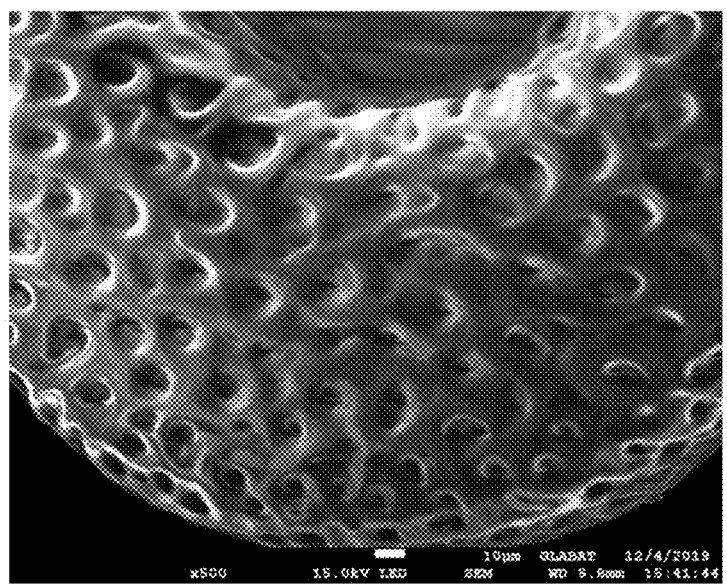
FIGS. 11-15 are electron micrographs of a degradable biomedical magnesium alloy drug-eluting vascular stent of Test Example 3 of the present invention.
Figure 12:
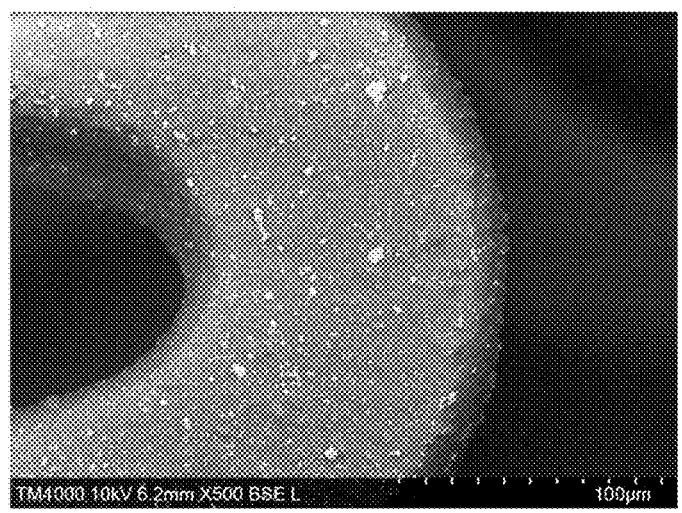
Figure 13:
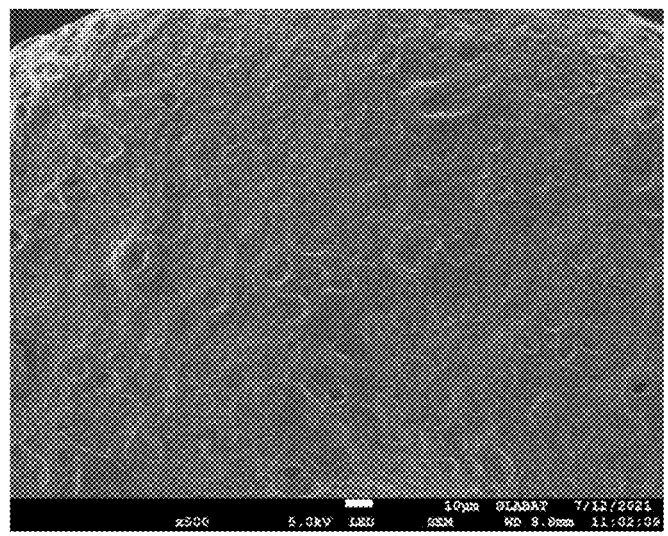
Figure 14:
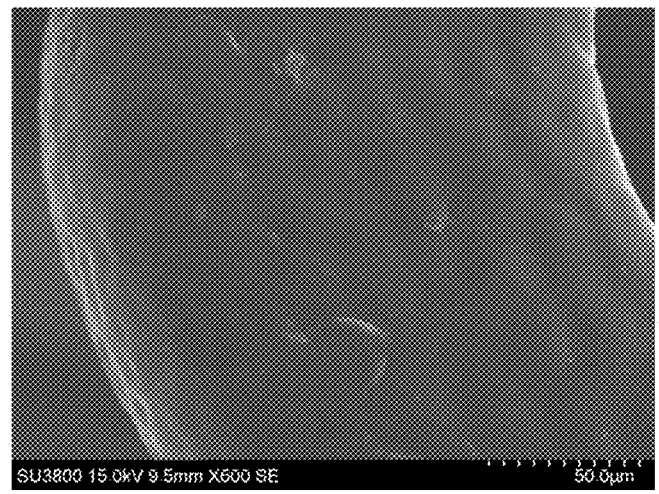
Figure 15:
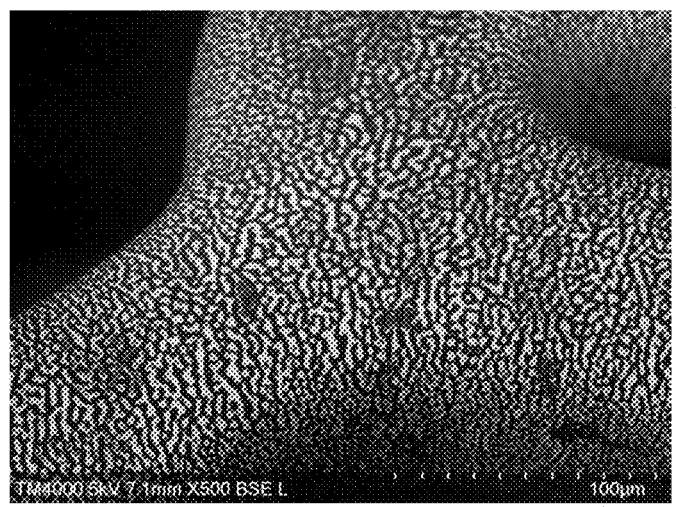

Evaluation of Stent Coating
Testing Method: Electron Microscope Observation.
Description of Results:

The electron microscope image of a polymer intermediate layer using the Stent Example 1 of the present application as a test sample is shown in FIG. 11. The electron microscope image of the polymer intermediate layer subjected to the magnesium fluoride hole sealing treatment is shown in FIG. 12. The electron microscope image of the sprayed polymer protective layer is shown in FIG. 13. The electron microscope image further subjected to the annealing treatment is shown in FIG. 14. The electron microscope image after coating the drug coating layer is shown in FIG. 15.

Figure 16:
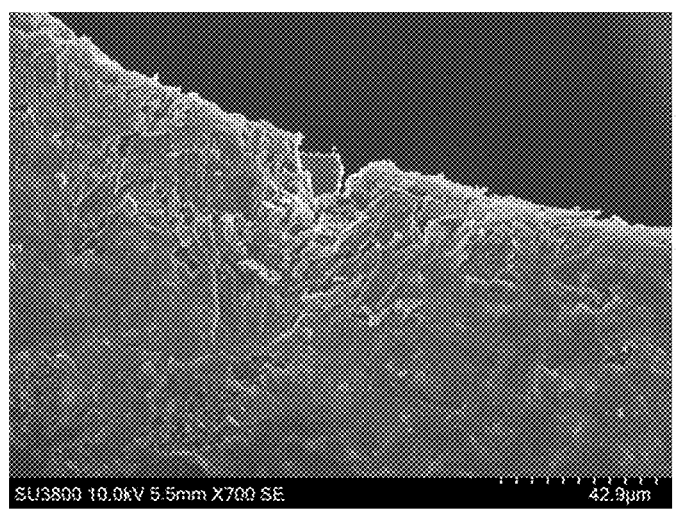
FIGS. 16 and 17 are electron micrographs of the comparative stent of Test Example 3 of the present invention.

Compared with the stent of the present application, only the fluorinated magnesium alloy stent (prepared according to the Stent Example 3 of the present application), although the surface is covered by a dense magnesium fluoride film layer, in the stent expansion process, the magnesium fluoride film layer in the stress concentration region is damaged by stress, and cracks are formed on the surface, which greatly reduces the corrosion resistance at this position, thereby generating serious local corrosion during the process of stent degradation. The electron microscope image of the film layer expansion damage is shown in FIG. 16.

Figure 17:
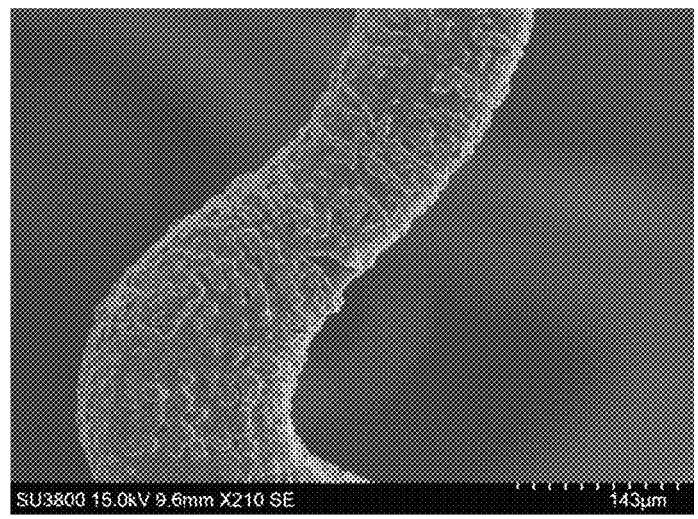

Compared with the stent of the present application, the polymer protective layer without annealing treatment (prepared according to the Stent Example 4 of the present application) has an insufficient binding force with the substrate, and the polymer protective layer forms many tiny holes due to volatilization of the organic solvent in the spraying process, which is prone to film damage when the stent is expanded. The electron microscope image is shown in FIG. 17. This damage may cause the area to lose its ability to isolate body fluid or blood, and cannot prevent ion exchange between the substrate and the implanted environment, thereby causing severe local corrosion in the early stage of degradation. Correspondingly, the local corrosion may cause serious loss of supporting force in the initial stage of the vascular stent, resulting in adverse consequences such as collapse of the vascular lumen.

Test Example 4

Figure 18:
FIGS. 18-20 are experimental results of the comparative stent of Test Example 4 of the present invention under near-physiological conditions, respectively.

Evaluation of degradation performance and supporting force of the stent under large deformation conditions in an in-vitro simulation environment Testing method: testing was performed according to the fatigue durability test method described in the "YY/T0808-2010 standard test method for in vitro pulsation durability of vascular stent".
Description of Results:

A degradable magnesium alloy bare stent was prepared according to the method of stent Example 2 (that is, no coating was applied outside the stent substrate). In the fatigue test of the obtained magnesium alloy bare stent after undergoing a large deformation process, degradation occurred in 36 h, the stent was broken, and there was no supporting force, as shown in FIG. 18. This test shows that under the near-physiological simulation condition, the magnesium alloy bare stent without protection measures has a very fast degradation rate with the action of large deformation process and continuous stress, which is much higher than the degradation rate in the common environment, such as in the immersion form of a simulated body fluid.

Figure 19:
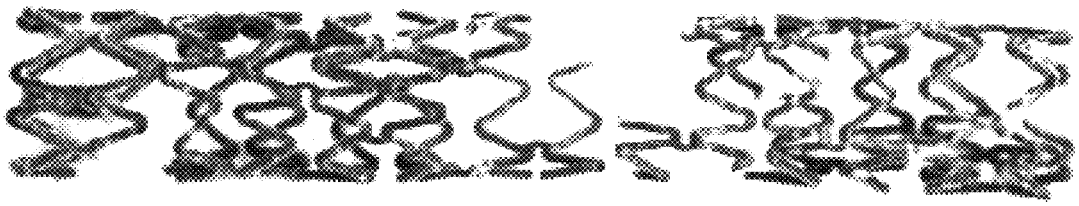

A degradable biomedical magnesium alloy drug-eluting vascular stent was prepared according to the method of Stent Example 3, and the degradation results showed that the stent had a large-area structure fallen off without supporting force, as shown in FIG. 19. This test shows that although the inorganic salt (magnesium fluoride) film layer formed by surface treatment, such as fluorination, can achieve certain corrosion resistance, the problem of damage of the film layer at which the stress is concentrated cannot be solved. Due to the severe local corrosion, a large amount of structural damage occurs in the initial stage of stent degradation.

Figure 20:
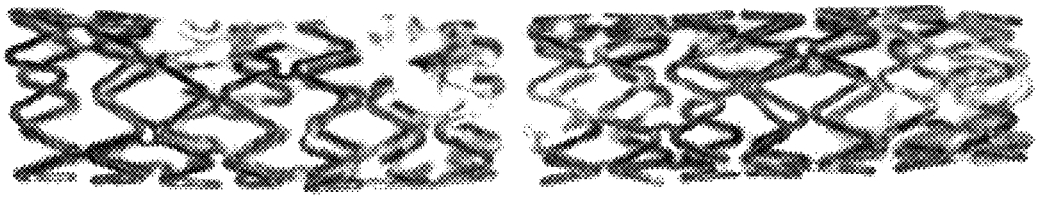

A degradable biomedical magnesium alloy drug-eluting vascular stent was prepared according to the method of Stent Example 4, and the degradation results showed that the stent was axially broken, the stress corrosion was severe, and there was no supporting force, as shown in FIG. 20. According to the test, although the corrosion resistance of the magnesium alloy vascular stent is improved to a certain extent through multi-layer protection treatment of a protection layer of magnesium fluoride and polymethyl methacrylate, the problem that a film layer is damaged after a large deformation process under a near-physiological condition still cannot be solved. Also, a severe local corrosion occurs at the initial stage of degradation, which causes the stent structure to fall off and lose the supporting force, resulting in adverse consequences such as vessel lumen collapse.

Figure 21:
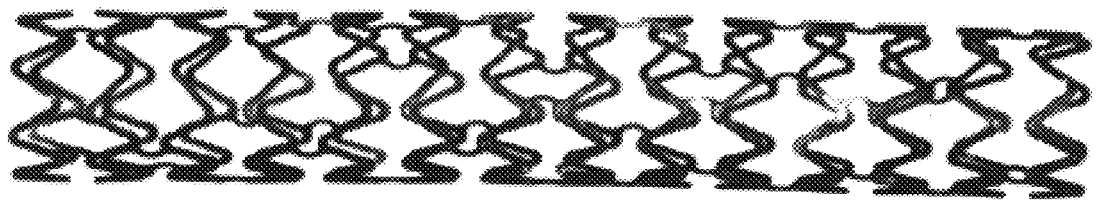
FIG. 21 is an experimental result diagram of the degradable biomedical magnesium alloy drug-eluting vascular stent of Test Example 4 of the present invention.

A degradable biomedical magnesium alloy drug-eluting vascular stent was prepared completely according to the method of Stent Example 1, and the degradation results after 3 months showed that the overall structure of the stent was not fallen off or broken, and there was only a small amount of local corrosion, as shown in FIG. 21.

The test shows that the composite coating of the degradable biomedical magnesium alloy drug-eluting vascular stent provided by the present invention can still play an effective protective role after undergoing a large deformation process under a near-physiological condition. Effective protection can still be provided in the stress-concentrated area, the degradation time is greatly prolonged, the local corrosion area is reduced, and the supporting force of the stent can be reserved for 3 months.

Test Example 5

Evaluation of Animal Experiments

Testing method: Firstly, an animal model was subjected to a pretreatment, that is, blood vessel dilation was carried out by using a disposable balloon dilation catheter at the blood vessel position where the stent was expected to be implanted, wherein the dilation ratio was 1.3-1.5 times of the diameter of the blood vessel. This caused damage to the blood vessel to a certain extent and a model of vascular stenosis developed 4 weeks after the pretreatment. Subsequently, the degradable biomedical magnesium alloy drug-eluting vascular stent was implanted at the position of vascular embolization, wherein the stent expansion ratio was 1.1 times of the diameter of the blood vessel. Follow-up visits were respectively carried out in 1 months and 6 months after operation, wherein the follow-up visits were angiography observation and intravascular OCT observation, for evaluating the intimal coverage degree, restenosis and degradation of the stent.

The degradable biomedical magnesium alloy drug-eluting vascular stent prepared completely according to the method of Stent Example 1 was tested in accordance with the testing method described in Test Example 5.

Figure 22:
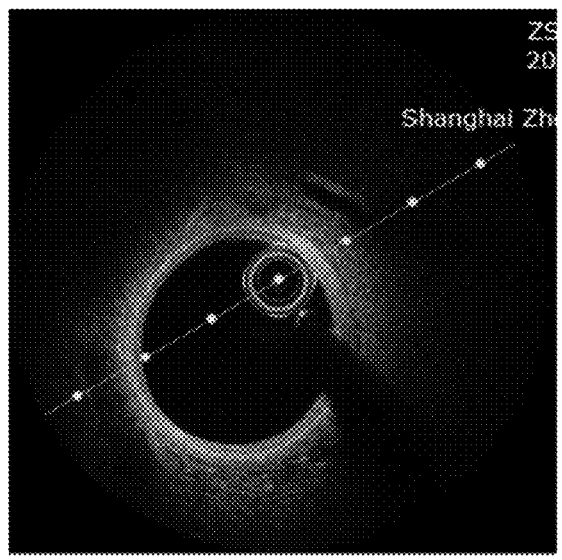
FIGS. 22-26 are OCT diagrams of Test Example 6 of the present invention.

Description of Results:

(1) The OCT photograph of a lumen where a porcine vessel is expected to be placed is shown in FIG. 22. The lumen is smooth and rounded.

Figure 23:
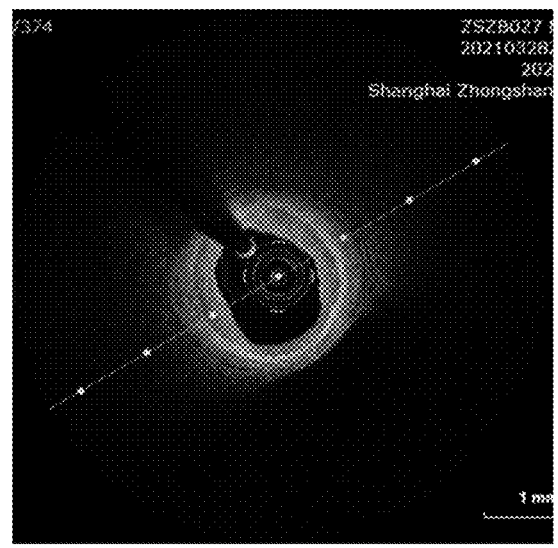

(2) The OCT photograph of the stenosis model after pre-treatment of the expected implantation position of the porcine vessel is shown in FIG. 23. The intimal hyperplasia is serious, the lumen is lost, and the stenosis rate is close to 50%, which satisfies the requirements of a vascular embolization model.

Figure 24:
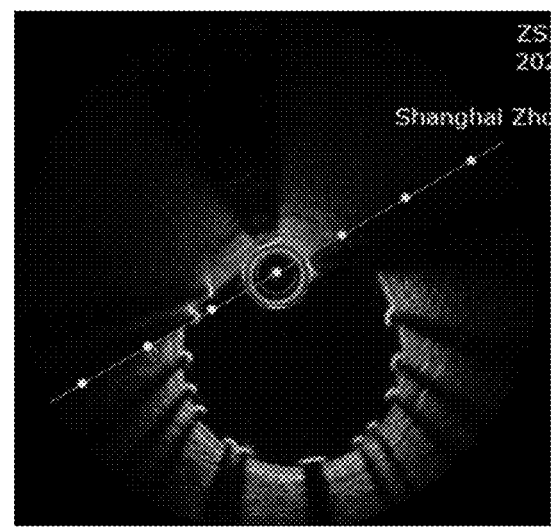

(3) The OCT photograph of the degradable biomedical magnesium alloy drug-eluting vascular stent provided by the present application after implantation is shown in FIG. 24. The stent is good in wall attachment without fracture and collapse of the lumen. The results show that the supporting force of the magnesium alloy stent provided by the present invention may satisfy the requirements.

Figure 25:
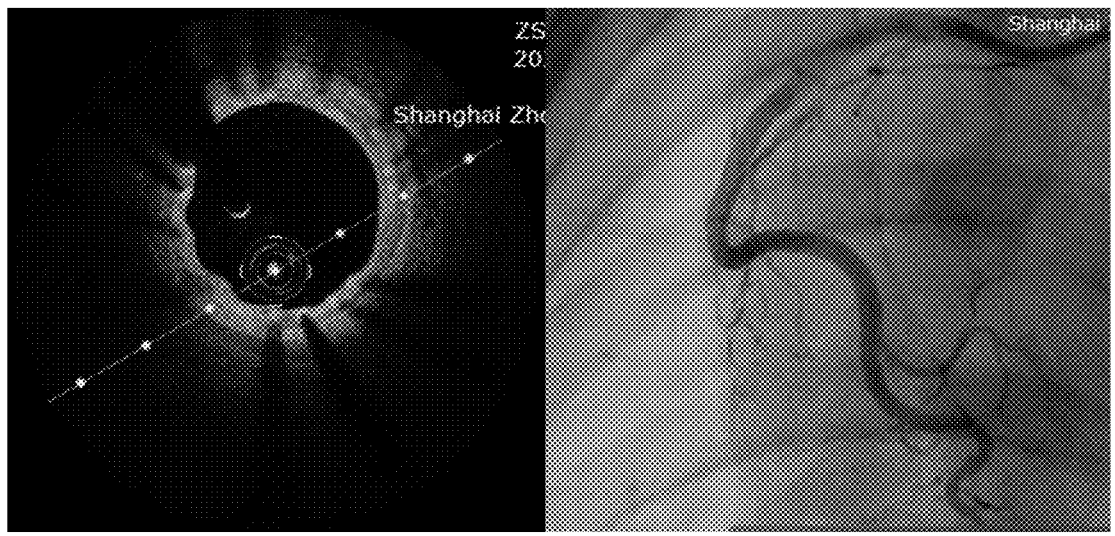

(4) The results of OCT and DSA angiography follow-up visit 1-month after the operation of the degradable biomedical magnesium alloy drug-eluting vascular stent provided by the present application are shown in FIG. 25. The angiography follow-up shows smooth blood flow and no stenosis, and the development point is clearly visible; the OCT follow-up shows that the intima is completely covered, the lumen is free of intima hyperplasia and inflammation, and the lumen loss rate is less than 5%. The results show that in the degradable biomedical magnesium alloy drug-eluting vascular stent provided by the present application, the polymer intermediate layer 7 and the polymer protective layer 6 can effectively control the degradation of the magnesium alloy substrate, and the drug coating layer 8 can achieve rapid endothelialization, inhibit smooth muscle proliferation, and adequately inhibit inflammation.

Figure 26:
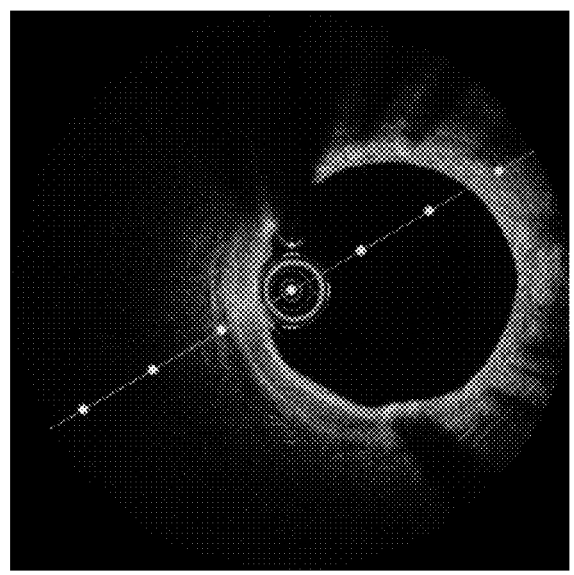

(5) The results of OCT follow-up visit 6-months after the operation the degradable biomedical magnesium alloy drug-eluting vascular stent provided by the present application are shown in FIG. 26. The lumen of the blood vessel still has no hyperplasia, no inflammation and no lumen loss, and the trabecular part of the stent is fuzzy and has been started to degrade. The results show that the degradable biomedical magnesium alloy drug-eluting vascular stent provided by the present application shows a good treatment effect in a large animal coronary stenosis model test, effectively prolongs the stent degradation time and supporting force retention time, is free of inflammation and hyperplasia, and has long-term safety.

Figure 27:
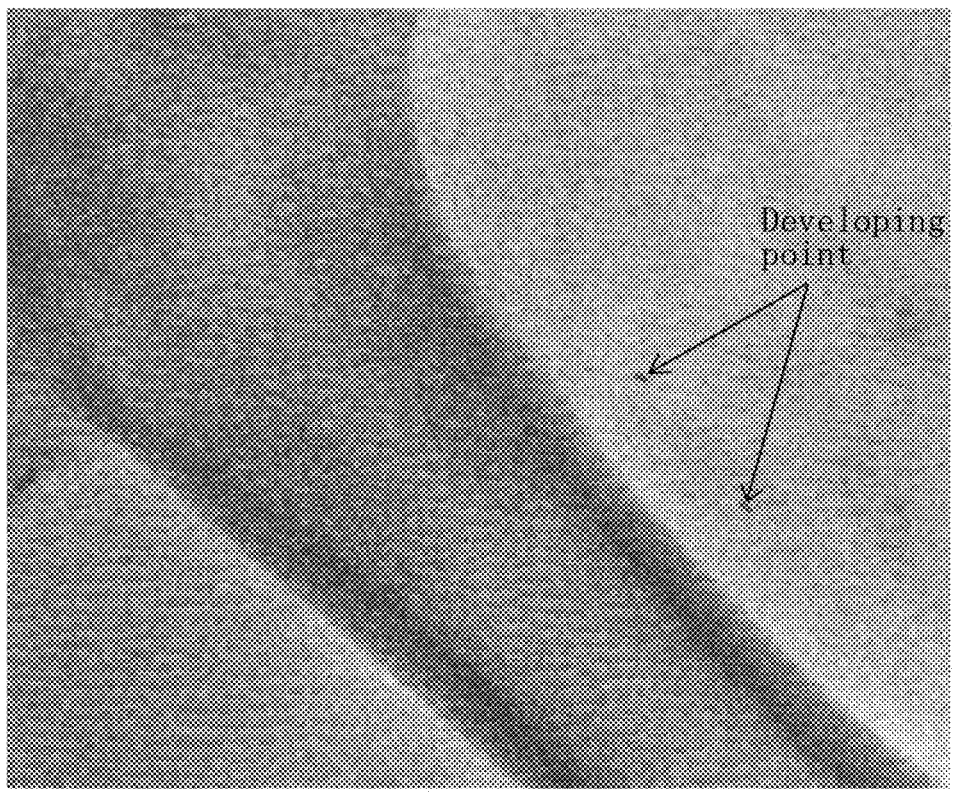
FIG. 27 is a radiopaque marker photograph of the stent of Test Example 6 of the present invention.

(6) The developability of the degradable biomedical magnesium alloy drug-eluting vascular stent provided by the present application is shown in FIG. 27. Under normal medical X-ray irradiation, the development points at the two ends of the stent are clearly visible. The two radiopaque marker points at the two ends are distributed at 90 degrees in the circumferential direction to ensure that the length and diameter parameters of the stent can be presented at different angles.

The invention claimed is:

1. A degradable biomedical magnesium alloy drug-eluting vascular stent, comprising a stent substrate, and a polymer intermediate layer, a polymer protective layer, and a drug coating layer arranged from inside to outside of the stent substrate, wherein the stent substrate comprises the following components in percentage by weight: 3.0-6.0% of Gd, 2.5-5.5% of Y, 0.3-1.0% of Zn, 0.2-1.0% of Zr and balance of Mg, with regard to a total weight of the stent substrate of 100%;
wherein the polymer of the polymer protective layer is polyvinylidene fluoride and a copolymer thereof; and the polymer protective layer has a thickness of 2 μm-10 μm;
wherein the vascular stent further comprises a drug coating layer provided on the outer surface of the polymer protective layer; the drug coating layer comprises a polymer carrier and an active drug; the active drug is a combination of tacrolimus and one selected from rapamycin and arsenic trioxide;
wherein the weight ratio of arsenic trioxide or rapamycin to tacrolimus is 1:2-4:1.

2. The degradable biomedical magnesium alloy drug-eluting vascular stent according to claim 1, wherein the components of the stent substrate comprise a plurality of annular supports, a connector and an end radiopaque marker structure; each support and the radiopaque marker structure are connected by the connector.

3. The degradable biomedical magnesium alloy drug-eluting vascular stent according to claim 2, wherein the components of the support comprise support units; each support unit is composed of a wave rod, two wave rod connecting sections and a circular arc body; the wave rod connecting sections are arranged at two ends of the wave rod, wherein the wave rod connecting section at one end is connected with one end of the two ends of the circular arc body of the same support unit, and the wave rod connecting section at the other end is connected with one end of the circular arc body of the adjacent support unit, thereby forming an annular support.

4. The degradable biomedical magnesium alloy drug-eluting vascular stent according to claim 3, wherein the width of the wave rod connecting section is 0.01 mm-0.05 mm smaller than the width of the wave rod.

5. The degradable biomedical magnesium alloy drug-eluting vascular stent according to claim 4, wherein the wave rod has a width of 0.1-0.18 mm and a length of 0.35-1.2 mm.

6. The degradable biomedical magnesium alloy drug-eluting vascular stent according to claim 3, wherein the circular arc body comprises an outer circular arc on an outer side and an inner circular arc on an inner side; both the centers of circles in which the inner circular arc and the outer circular arc are located on symmetry axes of two wave rods connected to the same circular arc body, and are not concentric; a center of the outer circular arc is located on a side of the center of the inner circular arc facing a vertex of the circular arc; and the distance between the inner circular arc and the outer circular arc is smallest at a joint with the wave rod connecting section, and gradually increases toward the vertex of the circular arc body until the symmetry axis is largest.

7. The degradable biomedical magnesium alloy drug-eluting vascular stent according to claim 6, wherein the outer circular arc has a diameter of 0.24-0.82 mm and a central angle of $\pi/2$-$3\pi/2$; the inner circular arc has a diameter of 0.02-0.60 mm and a central angle of $\pi/2$-$3\pi/2$; and the distance between centers of the outer circular arc and the inner circular arc is 0.01-0.05 mm.

8. The degradable biomedical magnesium alloy drug-eluting vascular stent according to claim 6, wherein the maximum distance between the inner circular arc and the outer circular arc is 0.01 mm-0.05 mm larger than the width of the wave rod, and the minimum distance is 0.01-0.05 mm smaller than the width of the wave rod.

9. The degradable biomedical magnesium alloy drug-eluting vascular stent according to claim 8, wherein the widths of the two ends of the wave rod connecting section are respectively the same as the width of the wave rod and the width of the end of the circular arc body, and the intermediate width is gradual transition.

10. The degradable biomedical magnesium alloy drug-eluting vascular stent according to claim 1, wherein the stent has a crimping diameter of 0.8 mm-2.8 mm, an expansion diameter of 2.0 mm-8.0 mm, and a length of 6 mm-150 mm.

11. The degradable biomedical magnesium alloy drug-eluting vascular stent according to claim 1, wherein the polymer intermediate layer is a polymer intermediate layer subjected to a magnesium fluoride hole sealing treatment; the polymer of the polymer intermediate layer is selected from one or more of polyvinylidene fluoride and a copolymer thereof, polymethyl methacrylate, and polybutyl methacrylate; and the polymer intermediate layer has a thickness of 100 nm-2000 nm.

12. The degradable biomedical magnesium alloy drug-eluting vascular stent according to claim 1, wherein the polymer material of the polymer carrier is selected from one or more of polylactic acid, racemic polylactic acid, polyglycolic acid, polylactic acid glycolic acid, polycaprolactone, and Poly(3-hydroxybutyrate-co-3-hydroxyvalerate) (PHBV).

13. The degradable biomedical magnesium alloy drug-eluting vascular stent according to claim 1, wherein the weight ratio of the polymer carrier to the active drug is 2:1-10:1.

14. The degradable biomedical magnesium alloy drug-eluting vascular stent according to claim 1, wherein in the drug coating layer, the content of arsenic trioxide or rapamycin is 2-20 µg/mm, and the content of tacrolimus is 1-25 µg/mm.

15. A preparing method of the degradable biomedical magnesium alloy drug-eluting vascular stent according to claim 2, comprising:
(1) processing the stent substrate, wherein the stent substrate comprises the following components in percentage by weight: 3.0-6.0% of GD, 2.25-5.55% of Zn, 0.2-1.0% or Zr and balance of Mg, with regard to a total weight of the stent substrate of 100%;
(2) coating the stent substrate with the a polymer intermediate layer;
(3) coating the polymer intermediate layer with the polymer protective layer, wherein the polymer of the polymer protective layer is polyvinylidene fluoride and a coplymer thereof; and the polymer protective layer has a thickness of 2 µm -10 µm; and
(4) coating a drug coating layer onto the polymer protective layer, wherein the drug coating layer provided on the outer surface of the polymer protective layer; the drug coating layer comprises a polymer carrier and an active drug; the active drug is a combination of tacrolimus and one selected from rapamycin and arsenic trioxide, wherein the weight ratio of arsenic trioxide or rapamycin to tacrolimus is 1:2-4:1, to produce the degradable biomedical magnesium alloy drug-eluting vascular stent.

16. The preparation method according to claim 15, wherein the step (2) comprises performing a fluorination hole sealing treatment on the polymer intermediate layer; the fluorination treatment comprises: immersing the stent substrate coated with the polymer intermediate layer in a fluorination treatment solution, and continuously stirring in a shaking bath at a rotation speed of 50-200 r/min; the fluorination treatment solution is prepared from a hydrofluoric acid solution and a potassium fluoride solution; the volume concentration of the hydrofluoric acid solution is 10-40%, the volume concentration of the potassium fluoride solution is 0.5-5 mol/L, and the volume ratio of the hydrofluoric acid solution to the potassium fluoride solution is 100:5-100:50; the temperature of the fluorination treatment solution is 18-85° C., and the treatment time is 30-600 min.

17. The preparation method according to claim 15, wherein the step (3) comprises subjecting the coated polymer protective stent to an annealing treatment; the annealing treatment comprises: heating the stent coated with the polymer protective layer to 60-200°° C. for 1-10 h under a vacuum condition, and taking out the stent after cooling to room temperature.

18. The preparation method according to claim 17, wherein the vacuum degree of the vacuum condition is not less than 1 × 10-3 Pa.

19. The preparation method according to claim 17, wherein the annealing treatment comprises: heating the stent coated with the polymer protective layer to 60-200° C. for 1-10 h under a vacuum condition, naturally cooling to below 50° C., introducing argon gas, continually cooling down to room temperature, and taking out the stent.

* * * * *